US005509915A

United States Patent [19]
Hanson et al.

[11] Patent Number: 5,509,915
[45] Date of Patent: Apr. 23, 1996

[54] THIN ABSORBENT ARTICLE HAVING RAPID UPTAKE OF LIQUID

[75] Inventors: William D. Hanson, Neenah; Lynn C. Brud; Shannon K. Byerly, both of Appleton, all of Wis.; Clifford J. Ellis, Woodstock, Ga.; Rob D. Everett, Appleton, Wis.; Barbara A. Gossen, Neenah, Wis.; Violet M. Grube, Appleton, Wis.; David G. Iwanski, Menasha, Wis.; David K. LeMahieu, Appleton, Wis.; Jian Qin, Appleton, Wis.; Robert A. Stevens, Appleton, Wis.; Tom K. Wentzel, Kimberly, Wis.; Sandra M. Yarbrough, Appleton, Wis.; David L. Zenker, Neenah, Wis.; MaryAnn Zunker, Oshkosh, Wis.

[73] Assignee: Kimberly-Clark Corporation, Neenah, Wis.

[21] Appl. No.: 96,654

[22] Filed: Jul. 22, 1993

Related U.S. Application Data

[63] Continuation of Ser. No. 757,760, Sep. 11, 1991, abandoned.
[51] Int. Cl.$^6$ ..................................................... A61F 13/20
[52] U.S. Cl. ............................................. 604/378; 604/367
[58] Field of Search .................................... 604/358, 378, 604/366–368, 381, 383, 385.1, 385.2

[56] References Cited

U.S. PATENT DOCUMENTS

| Re. 31,922 | 6/1985 | Mesek et al. | 604/385.2 |
|---|---|---|---|
| 2,761,449 | 9/1956 | Bletzinger | 128/285 |
| 3,016,599 | 1/1962 | Perry | 28/78 |
| 3,295,526 | 1/1967 | Sabee | 128/287 |
| 3,308,826 | 3/1967 | Blake | 128/290 |
| 3,369,544 | 2/1968 | Crockford | 128/285 |
| 3,509,881 | 5/1970 | Sabee | 128/287 |
| 3,523,536 | 8/1970 | Ruffo | 128/287 |

(List continued on next page.)

FOREIGN PATENT DOCUMENTS

| 1002304 | 12/1976 | Canada . |
|---|---|---|
| 1001831 | 12/1976 | Canada . |
| 1005335 | 2/1977 | Canada . |
| 1031105 | 5/1978 | Canada . |
| 1030798 | 5/1978 | Canada . |
| 1033554 | 6/1978 | Canada . |
| 1032386 | 6/1978 | Canada . |
| 1032301 | 6/1978 | Canada . |
| 1033903 | 7/1978 | Canada . |
| 1037368 | 8/1978 | Canada . |
| 1038554 | 9/1978 | Canada . |
| 1041252 | 10/1978 | Canada . |
| 1045127 | 12/1978 | Canada . |
| 1048832 | 2/1979 | Canada . |
| 1054987 | 5/1979 | Canada . |
| 1058125 | 7/1979 | Canada . |
| 1057457 | 7/1979 | Canada . |
| 1063088 | 9/1979 | Canada . |
| 1062898 | 9/1979 | Canada . |
| 1064635 | 10/1979 | Canada . |

(List continued on next page.)

Primary Examiner—Randall L. Green
Assistant Examiner—Robert Clarke
Attorney, Agent, or Firm—Paul Yee

[57] ABSTRACT

Generally stated, the present invention provides a distinctive absorbent article comprising a backsheet layer, and a topsheet layer which is disposed in facing relation with the backsheet layer. An absorbent body is interposed between the backsheet layer and topsheet layer. The absorbent body includes a retention portion which comprises a matrix of substantially hydrophilic fibers having a distribution of high-absorbency particulate material therein. The hydrophilic fibers and high-absorbency particles can be provided in a fiber-to-particle weight ratio within the range of about 70:30 to about 30:70. A surge management layer, comprising bicomponent fibers having a denier of not more than about 3 d, is located adjacent at least one major, facing surface of the topsheet layer, and can cooperate with the article components to provide for a liquid Penetration Rate index of not less than about 2.67 ml/sec.

52 Claims, 8 Drawing Sheets

U.S. PATENT DOCUMENTS

| | | | |
|---|---|---|---|
| 1063918 | 10/1979 | Canada . | |
| 1065554 | 11/1979 | Canada . | |
| 3,592,194 | 7/1971 | Duncan | 128/287 |
| 3,595,235 | 7/1971 | Jespersen | 128/284 |
| 3,612,055 | 10/1971 | Mesek et al. | 128/287 |
| 3,636,952 | 1/1972 | George | 128/287 |
| 3,661,680 | 5/1972 | Gore | 156/467 |
| 3,663,348 | 5/1972 | Liloia et al. | 161/116 |
| 3,665,921 | 5/1972 | Stumpf | 128/287 |
| 3,730,184 | 5/1973 | Mesek | 128/287 |
| 3,768,118 | 10/1973 | Ruffo et al. | 19/156.3 |
| 3,768,480 | 10/1973 | Mesek et al. | 128/287 |
| 3,772,417 | 11/1973 | Vogt | 264/230 |
| 3,777,758 | 12/1973 | Mesek | 128/284 |
| 3,806,289 | 4/1974 | Schwarz | 425/72 |
| 3,837,343 | 9/1974 | Mesek | 128/287 |
| 3,871,378 | 3/1975 | Duncan et al. | 128/290 |
| 3,908,659 | 9/1975 | Wehrmeyer et al. | 128/287 |
| 3,927,673 | 12/1975 | Taylor | 128/287 |
| 3,945,386 | 3/1976 | Anczurowski et al. | 128/287 |
| 3,952,124 | 4/1976 | Mesek | 428/218 |
| 3,965,905 | 6/1976 | Schoenholz et al. | 128/285 |
| 3,965,906 | 6/1976 | Karami | 128/287 |
| 3,978,185 | 8/1976 | Buntin et al. | 264/93 |
| 3,987,792 | 10/1976 | Hernandez et al. | 128/284 |
| 4,014,341 | 3/1977 | Karami | 128/287 |
| 4,018,862 | 4/1977 | Saito | 264/137 |
| 4,041,951 | 8/1977 | Sanford | 128/287 |
| 4,044,768 | 8/1977 | Mesek et al. | 128/287 |
| 4,045,833 | 9/1977 | Mesek et al. | 5/335 |
| 4,069,822 | 1/1978 | Buell | 128/294 |
| 4,077,410 | 3/1978 | Butterworth et al. | 128/287 |
| 4,103,058 | 7/1978 | Humlicek | 428/171 |
| 4,118,531 | 10/1978 | Hauser | 428/224 |
| 4,147,580 | 4/1979 | Buell | 156/291 |
| 4,212,302 | 7/1980 | Karami | 128/287 |
| 4,216,772 | 8/1980 | Tsuchiya et al. | 128/284 |
| 4,223,677 | 9/1980 | Anderson | 128/287 |
| 4,232,674 | 11/1980 | Melican | 128/287 |
| 4,238,175 | 12/1980 | Fujii et al. | 425/83.1 |
| 4,259,958 | 4/1981 | Goodbar | 128/287 |
| 4,261,782 | 4/1981 | Teed | 156/361 |
| 4,285,342 | 8/1981 | Mesek | 128/287 |
| 4,304,234 | 12/1981 | Hartmann | 128/287 |
| 4,324,247 | 4/1982 | Aziz | 128/287 |
| 4,325,372 | 4/1982 | Teed | 128/287 |
| 4,338,371 | 7/1982 | Dawn et al. | 428/283 |
| 4,364,992 | 12/1982 | Ito et al. | 428/283 |
| 4,372,312 | 2/1983 | Fendler et al. | 128/290 R |
| 4,374,888 | 2/1983 | Bornslaeger | 428/198 |
| 4,381,611 | 5/1983 | Wishman | 34/9 |
| 4,381,782 | 5/1983 | Mazurak et al. | 604/368 |
| 4,392,861 | 7/1983 | Butterworth et al. | 604/366 |
| 4,392,862 | 7/1983 | Marsan et al. | 604/366 |
| 4,397,644 | 8/1983 | Matthews et al. | 604/366 |
| 4,405,325 | 9/1983 | Antlfinger et al. | 604/370 |
| 4,413,032 | 11/1983 | Hartmann et al. | 428/288 |
| 4,421,813 | 12/1983 | Athey | 428/195 |
| 4,436,780 | 3/1984 | Hotchkiss et al. | 428/198 |
| 4,461,621 | 7/1984 | Karami et al. | 604/368 |
| 4,468,428 | 8/1984 | Early et al. | 428/221 |
| 4,480,000 | 10/1984 | Watanabe et al. | 428/284 |
| 4,496,358 | 1/1985 | Karami et al. | 604/379 |
| 4,500,315 | 2/1985 | Pieniak et al. | 604/379 |
| 4,500,384 | 2/1985 | Tomioka et al. | 156/290 |
| 4,501,586 | 2/1985 | Holtman | 604/380 |
| 4,519,798 | 5/1985 | Dinius | 604/358 |
| 4,519,799 | 5/1985 | Sakurai et al. | 604/366 |
| 4,531,945 | 7/1985 | Allison | 604/378 |
| 4,535,020 | 8/1985 | Thomas et al. | 428/131 |
| 4,537,590 | 8/1985 | Pieniak et al. | 604/379 |
| 4,540,414 | 9/1985 | Wishman | 604/378 |
| 4,540,454 | 9/1985 | Pieniak et al. | 156/62.2 |
| 4,550,725 | 11/1985 | Wishman | 128/155 |
| 4,551,143 | 11/1985 | Cook et al. | 604/371 |
| 4,552,603 | 11/1985 | Harris, Jr. et al. | 156/167 |
| 4,557,777 | 12/1985 | Sabee | 156/201 |
| 4,559,051 | 12/1985 | Hanson | 604/385 R |
| 4,560,372 | 12/1985 | Pieniak | 604/369 |
| 4,573,986 | 3/1986 | Minetola et al. | 604/366 |
| 4,573,988 | 3/1986 | Pieniak et al. | 604/379 |
| 4,578,066 | 3/1986 | O'Connor | 604/366 |
| 4,578,070 | 3/1986 | Holtman | 604/378 |
| 4,578,414 | 3/1986 | Sawyer et al. | 524/310 |
| 4,590,114 | 5/1986 | Holtman | 428/171 |
| 4,608,292 | 8/1986 | Lassen | 428/131 |
| 4,623,340 | 11/1986 | Luceri | 604/385 R |
| 4,623,576 | 11/1986 | Lloyd et al. | 428/171 |
| 4,626,252 | 12/1986 | Nishizawa et al. | 604/370 |
| 4,636,209 | 1/1987 | Lassen | 604/378 |
| 4,654,040 | 3/1987 | Luceri | 604/385 R |
| 4,655,757 | 4/1987 | McFarland et al. | 604/366 |
| 4,673,402 | 6/1987 | Weisman et al. | 604/368 |
| 4,675,013 | 6/1987 | Ruffo | 604/366 |
| 4,681,577 | 7/1987 | Stern et al. | 604/378 |
| 4,699,619 | 10/1987 | Bernardin | 604/378 |
| 4,699,620 | 10/1987 | Bernardin | 604/385 A |
| 4,704,112 | 11/1987 | Suzuki et al. | 604/378 |
| 4,707,398 | 11/1987 | Boggs | 428/224 |
| 4,714,647 | 12/1987 | Shipp, Jr. et al. | 428/212 |
| 4,732,809 | 3/1988 | Harris, Jr. et al. | 428/373 |
| 4,735,624 | 4/1988 | Mazars | 604/378 |
| 4,738,676 | 4/1988 | Osborn, III | 604/385 R |
| 4,755,178 | 7/1988 | Insley et al. | 604/367 |
| 4,755,179 | 7/1988 | Shiba et al. | 604/370 |
| 4,794,034 | 12/1988 | Nishizawa et al. | 428/218 |
| 4,798,603 | 1/1989 | Meyer et al. | 604/378 |
| 4,816,025 | 3/1989 | Foreman | 604/378 |
| 4,830,904 | 5/1989 | Gessner et al. | 428/219 |
| 4,851,284 | 7/1989 | Yamanoi et al. | 428/284 |
| 4,883,707 | 11/1989 | Newkirk | 428/219 |
| 4,917,746 | 4/1990 | Kons et al. | 156/164 |
| 4,923,454 | 5/1990 | Seymour et al. | 604/368 |
| 4,950,264 | 8/1990 | Osborn, III | 604/385.1 |
| 4,988,344 | 1/1991 | Reising et al. | 604/368 |
| 4,988,345 | 1/1991 | Reising | 604/368 |
| 5,037,409 | 8/1991 | Chen et al. | 604/358 |
| 5,098,423 | 3/1992 | Pieniak et al. | 604/385.1 |
| 5,135,521 | 8/1992 | Luceri et al. | 604/370 |
| 5,334,152 | 8/1994 | Nomura et al. | 604/385.2 |
| B1 3,860,003 | 4/1989 | Buell | 604/385.2 |

FOREIGN PATENT DOCUMENTS

| | | |
|---|---|---|
| 1071943 | 2/1980 | Canada . |
| 1074475 | 3/1980 | Canada . |
| 1072872 | 3/1980 | Canada . |
| 1082086 | 7/1980 | Canada . |
| 1082087 | 7/1980 | Canada . |
| 1082089 | 7/1980 | Canada . |
| 1085810 | 9/1980 | Canada . |
| 1091854 | 12/1980 | Canada . |
| 1092332 | 12/1980 | Canada . |
| 1090995 | 12/1980 | Canada . |
| 1097451 | 3/1981 | Canada . |
| 1100706 | 5/1981 | Canada . |
| 1103869 | 6/1981 | Canada . |
| 1104002 | 6/1981 | Canada . |
| 1110007 | 10/1981 | Canada . |
| 1124006 | 5/1982 | Canada . |
| 1123151 | 5/1982 | Canada . |
| 1127831 | 7/1982 | Canada . |
| 1128411 | 7/1982 | Canada . |

| | | | | | | |
|---|---|---|---|---|---|---|
| 1133866 | 10/1982 | Canada . | | 1212369 | 10/1986 | Canada . |
| 1134126 | 10/1982 | Canada . | | 1215824 | 12/1986 | Canada . |
| 1134551 | 11/1982 | Canada . | | 1214901 | 12/1986 | Canada . |
| 1135452 | 11/1982 | Canada . | | 1217170 | 1/1987 | Canada . |
| 1137044 | 12/1982 | Canada . | | 1216702 | 1/1987 | Canada . |
| 1137253 | 12/1982 | Canada . | | 1220623 | 4/1987 | Canada . |
| 1140511 | 2/1983 | Canada . | | 1222103 | 5/1987 | Canada . |
| 1143506 | 3/1983 | Canada . | | 1223402 | 6/1987 | Canada . |
| 1146129 | 5/1983 | Canada . | | 1223436 | 6/1987 | Canada . |
| 1148701 | 6/1983 | Canada . | | 1223188 | 6/1987 | Canada . |
| 1148302 | 6/1983 | Canada . | | 1226120 | 9/1987 | Canada . |
| 1148301 | 6/1983 | Canada . | | 1228257 | 10/1987 | Canada . |
| 1150488 | 7/1983 | Canada . | | 1228004 | 10/1987 | Canada . |
| 1149593 | 7/1983 | Canada . | | 1231325 | 1/1988 | Canada . |
| 1149103 | 7/1983 | Canada . | | 1234253 | 3/1988 | Canada . |
| 1149102 | 7/1983 | Canada . | | 1236074 | 5/1988 | Canada . |
| 1149101 | 7/1983 | Canada . | | 1236056 | 5/1988 | Canada . |
| 1152701 | 8/1983 | Canada . | | 1238151 | 6/1988 | Canada . |
| 1152702 | 8/1983 | Canada . | | 1238882 | 7/1988 | Canada . |
| 1151352 | 8/1983 | Canada . | | 1239012 | 7/1988 | Canada . |
| 1150904 | 8/1983 | Canada . | | 1241570 | 9/1988 | Canada . |
| 1153502 | 9/1983 | Canada . | | 1241504 | 9/1988 | Canada . |
| 1154238 | 9/1983 | Canada . | | 1242629 | 10/1988 | Canada . |
| 1153345 | 9/1983 | Canada . | | 1245001 | 11/1988 | Canada . |
| 1153153 | 9/1983 | Canada . | | 1245004 | 11/1988 | Canada . |
| 1153152 | 9/1983 | Canada . | | 1246334 | 12/1988 | Canada . |
| 1155253 | 10/1983 | Canada . | | 1246979 | 12/1988 | Canada . |
| 1154901 | 10/1983 | Canada . | | 1247302 | 12/1988 | Canada . |
| 1165946 | 4/1984 | Canada . | | 1247803 | 1/1989 | Canada . |
| 1168137 | 5/1984 | Canada . | | 1250136 | 2/1989 | Canada . |
| 1174837 | 9/1984 | Canada . | | 1251901 | 4/1989 | Canada . |
| 1174835 | 9/1984 | Canada . | | 1251902 | 4/1989 | Canada . |
| 1174836 | 9/1984 | Canada . | | 1251922 | 4/1989 | Canada . |
| 1176401 | 10/1984 | Canada . | | 1252953 | 4/1989 | Canada . |
| 1175602 | 10/1984 | Canada . | | 1267271 | 4/1989 | Canada . |
| 1175603 | 10/1984 | Canada . | | 1252952 | 4/1989 | Canada . |
| 1177701 | 11/1984 | Canada . | | 1253319 | 5/1989 | Canada . |
| 1177633 | 11/1984 | Canada . | | 1253752 | 5/1989 | Canada . |
| 1181201 | 1/1985 | Canada . | | 1255887 | 6/1989 | Canada . |
| 1181044 | 1/1985 | Canada . | | 1257751 | 7/1989 | Canada . |
| 1180173 | 1/1985 | Canada . | | 1261102 | 9/1989 | Canada . |
| 1180887 | 1/1985 | Canada . | | 1259175 | 9/1989 | Canada . |
| 1182692 | 2/1985 | Canada . | | 1259151 | 9/1989 | Canada . |
| 1182601 | 2/1985 | Canada . | | 1262301 | 10/1989 | Canada . |
| 1182602 | 2/1985 | Canada . | | 1263064 | 11/1989 | Canada . |
| 1182604 | 2/1985 | Canada ................................ 604/378 | | 1265301 | 2/1990 | Canada . |
| 1183303 | 3/1985 | Canada . | | 1266745 | 3/1990 | Canada . |
| 1183306 | 3/1985 | Canada . | | 2003458 | 5/1990 | Canada . |
| 1184352 | 3/1985 | Canada . | | 2002821 | 5/1990 | Canada . |
| 1183304 | 3/1985 | Canada . | | 2004290 | 5/1990 | Canada . |
| 1185051 | 4/1985 | Canada . | | 2002928 | 5/1990 | Canada . |
| 1186184 | 4/1985 | Canada . | | 2004492 | 6/1990 | Canada . |
| 1186288 | 4/1985 | Canada . | | 2009452 | 8/1990 | Canada . |
| 1187685 | 5/1985 | Canada . | | 1273188 | 8/1990 | Canada . |
| 1187684 | 5/1985 | Canada . | | 1272851 | 8/1990 | Canada . |
| 1186571 | 5/1985 | Canada . | | 1274052 | 9/1990 | Canada . |
| 1186852 | 5/1985 | Canada . | | 2012316 | 9/1990 | Canada . |
| 1187391 | 5/1985 | Canada . | | 2011672 | 9/1990 | Canada . |
| 1189252 | 6/1985 | Canada . | | 2028853 | 9/1990 | Canada . |
| 1190134 | 7/1985 | Canada . | | 2013943 | 10/1990 | Canada . |
| 1190031 | 7/1985 | Canada . | | 2013182 | 10/1990 | Canada . |
| 1193155 | 9/1985 | Canada . | | 2009956 | 10/1990 | Canada . |
| 1195804 | 10/1985 | Canada . | | 2012002 | 10/1990 | Canada . |
| 1194281 | 10/1985 | Canada . | | 2013441 | 10/1990 | Canada . |
| 1198045 | 12/1985 | Canada . | | 2015581 | 10/1990 | Canada . |
| 1203351 | 4/1986 | Canada . | | 2013115 | 10/1990 | Canada . |
| 1207104 | 7/1986 | Canada . | | 1275789 | 11/1990 | Canada . |
| 1209753 | 8/1986 | Canada . | | 2057070 | 11/1990 | Canada . |
| 1209752 | 8/1986 | Canada . | | 2015532 | 11/1990 | Canada . |
| 1211902 | 9/1986 | Canada . | | 2017609 | 11/1990 | Canada . |
| 1211745 | 9/1986 | Canada . | | 2055605 | 12/1990 | Canada . |
| 1211602 | 9/1986 | Canada . | | 1277577 | 12/1990 | Canada . |

| | | | | | | |
|---|---|---|---|---|---|---|
| 2016733 | 12/1990 | Canada . | | 2054269 | 6/1992 | Canada . |
| 1279152 | 1/1991 | Canada . | | 1302654 | 6/1992 | Canada . |
| 2021239 | 1/1991 | Canada . | | 1303794 | 6/1992 | Canada . |
| 1279944 | 2/1991 | Canada . | | 1305290 | 7/1992 | Canada . |
| 2023038 | 2/1991 | Canada . | | 1305289 | 7/1992 | Canada . |
| 2064871 | 2/1991 | Canada . | | 2058744 | 7/1992 | Canada . |
| 2022629 | 2/1991 | Canada . | | 1304567 | 7/1992 | Canada . |
| 1280062 | 2/1991 | Canada . | | 1304923 | 7/1992 | Canada . |
| 1280551 | 2/1991 | Canada . | | 1305291 | 7/1992 | Canada . |
| 2023680 | 3/1991 | Canada . | | 1305293 | 7/1992 | Canada . |
| 1280879 | 3/1991 | Canada . | | 2056960 | 8/1992 | Canada . |
| 2022057 | 3/1991 | Canada . | | 1305952 | 8/1992 | Canada . |
| 2028510 | 4/1991 | Canada . | | 1306721 | 8/1992 | Canada . |
| 2066651 | 4/1991 | Canada . | | 1307923 | 9/1992 | Canada . |
| 1282203 | 4/1991 | Canada . | | 1307244 | 9/1992 | Canada . |
| 1282554 | 4/1991 | Canada . | | 1307500 | 9/1992 | Canada . |
| 2066411 | 5/1991 | Canada . | | 2066483 | 10/1992 | Canada . |
| 2029014 | 5/1991 | Canada . | | 2064950 | 10/1992 | Canada . |
| 2027777 | 5/1991 | Canada . | | 1309391 | 10/1992 | Canada . |
| 1284424 | 5/1991 | Canada . | | 1309003 | 10/1992 | Canada . |
| 2027805 | 5/1991 | Canada . | | 1310481 | 11/1992 | Canada . |
| 2029129 | 5/1991 | Canada . | | 1309851 | 11/1992 | Canada . |
| 1285130 | 6/1991 | Canada . | | 1310308 | 11/1992 | Canada . |
| 2033002 | 6/1991 | Canada . | | 2067687 | 12/1992 | Canada . |
| 1285129 | 6/1991 | Canada . | | 1311879 | 12/1992 | Canada . |
| 2072650 | 6/1991 | Canada . | | 2044768 | 12/1992 | Canada . |
| 2024472 | 6/1991 | Canada . | | 2065220 | 12/1992 | Canada . |
| 2032061 | 6/1991 | Canada . | | 2070335 | 1/1993 | Canada . |
| 2072990 | 6/1991 | Canada . | | 2073123 | 1/1993 | Canada . |
| 2032388 | 6/1991 | Canada . | | 2074649 | 2/1993 | Canada . |
| 2034111 | 7/1991 | Canada . | | 2079134 | 3/1993 | Canada . |
| 1286857 | 7/1991 | Canada . | | 1317736 | 5/1993 | Canada . |
| 2033365 | 7/1991 | Canada . | | 2084040 | 5/1993 | Canada . |
| 1285701 | 7/1991 | Canada . | | 1319486 | 6/1993 | Canada . |
| 1287700 | 8/1991 | Canada . | | 2084841 | 6/1993 | Canada . |
| 1288584 | 9/1991 | Canada . | | 0070163 | 1/1983 | European Pat. Off. . |
| 1288922 | 9/1991 | Canada . | | 0070164 | 1/1983 | European Pat. Off. . |
| 2039011 | 9/1991 | Canada . | | 0108637 | 5/1984 | European Pat. Off. . |
| 1289298 | 9/1991 | Canada . | | 0165807 | 12/1985 | European Pat. Off. . |
| 2037580 | 9/1991 | Canada . | | 0173058A3 | 3/1986 | European Pat. Off. . |
| 1288200 | 9/1991 | Canada . | | 0174775 | 3/1986 | European Pat. Off. . |
| 2041119 | 10/1991 | Canada . | | 0193309A1 | 9/1986 | European Pat. Off. . |
| 1290502 | 10/1991 | Canada . | | 0254476 | 1/1988 | European Pat. Off. . |
| 1291325 | 10/1991 | Canada . | | 0286543A2 | 10/1988 | European Pat. Off. . |
| 1291328 | 10/1991 | Canada . | | 0317058A1 | 5/1989 | European Pat. Off. . |
| 1290501 | 10/1991 | Canada . | | 0359501A2 | 3/1990 | European Pat. Off. . |
| 2043016 | 11/1991 | Canada . | | 0377212A2 | 7/1990 | European Pat. Off. . |
| 1293433 | 12/1991 | Canada . | | 0397110A2 | 11/1990 | European Pat. Off. . |
| 2045116 | 12/1991 | Canada . | | 0439962A1 | 8/1991 | European Pat. Off. . |
| 1294390 | 1/1992 | Canada . | | 3525379A1 | 1/1987 | Germany . |
| 1294391 | 1/1992 | Canada . | | 61-2854 | 1/1986 | Japan . |
| 1295927 | 2/1992 | Canada . | | 1308935 | 3/1973 | United Kingdom . |
| 1295301 | 2/1992 | Canada . | | 1389891 | 4/1975 | United Kingdom . |
| 1297638 | 3/1992 | Canada . | | 1402327 | 8/1975 | United Kingdom . |
| 1296953 | 3/1992 | Canada . | | 1547524 | 6/1979 | United Kingdom . |
| 1296875 | 3/1992 | Canada . | | 2023068 | 12/1979 | United Kingdom . |
| 2050782 | 3/1992 | Canada . | | 2055586 | 3/1981 | United Kingdom . |
| 2049861 | 3/1992 | Canada . | | 2063683 | 6/1981 | United Kingdom . |
| 1296489 | 3/1992 | Canada . | | 2087240 | 5/1982 | United Kingdom . |
| 1298934 | 4/1992 | Canada . | | 2089214 | 6/1982 | United Kingdom . |
| 1315485 | 4/1992 | Canada . | | 2101038 | 1/1983 | United Kingdom . |
| 1298768 | 4/1992 | Canada . | | 2131699 | 6/1984 | United Kingdom . |
| 1300572 | 5/1992 | Canada . | | 2145661 | 4/1985 | United Kingdom . |
| 1301127 | 5/1992 | Canada . | | 2170108 | 7/1986 | United Kingdom . |
| 1301440 | 5/1992 | Canada . | | 2214201 | 8/1989 | United Kingdom . |
| 1300128 | 5/1992 | Canada . | | WO80/01455 | 7/1980 | WIPO . |
| 2057521 | 6/1992 | Canada . | | WO86/05661 | 9/1985 | WIPO . |
| 1302986 | 6/1992 | Canada . | | WO91/11164 | 2/1991 | WIPO . |
| 1303830 | 6/1992 | Canada . | | | | |

ABSORBENT ARTICLE HAVING
RAPID UPTAKE OF LIQUID

This is a continuation of applications(s) Ser. No. 07/757,760 filed on Sep. 11, 1991, now abandoned.

TECHNICAL FIELD

This invention relates to absorbent articles, particularly absorbent structures which are useful in personal care products. Note particularly, the invention relates to absorbent articles which are designed for the rapid uptake, distribution and retention of repeated liquid surges into the absorbent portion of the article.

BACKGROUND OF THE INVENTION

Desired performance objectives of personal care absorbent products include low leakage from the product and a dry feel to the wearer. However, absorbent products commonly fail before the total absorbent capacity of the product is utilized. An absorbent garment, such as an incontinence garment or disposable diaper, often leaks at the leg, top-front or top-back areas of the diaper. Leakage can occur due to a variety of shortcomings in the product, one being an insufficient rate of fluid uptake by the absorbent system, especially on the second or third liquid surges.

It has been found that urination can occur at rates as high as 15 to 20 milliliters per second and at velocities as high as 280 centimeters per second. Conventional diaper absorbent structures, such as those comprising admixtures of absorbent gelling particles and cellulosic fluffed pulp, may initially uptake fluid at rates of only about 8 milliliters per second or less, depending somewhat on the web density and concentration of gelling particulates. The initial uptake rates, however, for conventional absorbent structures can deteriorate once they have already received liquid surges into their structures. The above disparity between liquid delivery and uptake rates can result in excessive pooling on the surface of the fabric before it is taken up by the structure. In the meantime, pooled fluid can leak from the leg opening of the diaper and soil the outer clothing or bedding of the wearer.

Attempts to alleviate leakage include providing physical barriers with elastic leg gathers and changing the amount or configuration of the absorbent material at the zone of the structure into which the liquid surges typically occur. Absorbent gelling particles have also been included to increase the liquid holding capacity in various regions of the absorbent structure.

Absorbent articles have typically employed various types of absorbent pads composed of cellulosic fibers. For example, U.S. Pat. No. 3,523,536 to Ruffo discloses an absorbent fibrous web of predominantly shorter fibers intermixed with relatively longer fibers For purposes of stabilizing the web. U.S. Pat. No. 3,768,118 to Ruffo, et al. relates to a process for blending longer and shorter fibers. U.S. Pat. No. 3,663,348 to Liloia, et al. discloses an absorbent product in which a disclosed Fabric serves as a bodyside, Fluid pervious liner material, and an absorbent core includes a loosely compacted cellulose batt with a densified layer on one side.

Particular absorbent garments have been configured to control the distribution of absorbed liquids. U.S. Pat. No. 4,578,070 to Holtman discloses incontinence pads which include a bilayer, corrugated nonwoven structure. U.S. Pat. No. 4,681,577 to Stern and Holtman discloses incontinence pads placed in a liquid-impermeable, flexible shell. The absorbent structure disclosed in the '577 patent includes either a corrugated or uncorrugated version of the bilayer nonwoven structure disclosed in the '070 patent, located in the front portion of the product. A second resilient, open structure, such as a resilient nonwoven or open cell foam, in the back portion is further disclosed for the purpose of providing Fecal waste containment.

U.S. Pat. No. 4,699,619 to Bernardin discloses another cellulosic absorbent structure which can comprise a multilayer core arrangement wherein a top layer has a greater pore size than that of an underlying layer. The pore size gradient between the core layers can be achieved in various ways, for example, by using webs of different densities or webs with a common density but formed from fibers of different sizes. A portion of superabsorbent material can also be placed at various locations within the absorbent structure.

U.S. Pat No. 4,585,448 issued Apr. 29, 1986, to K. Enloe describes a disposable garment comprising an integral absorbent pad disposed between a liquid pervious body-side liner sheet and a liquid impervious backing sheet. The absorbent pad is provided with a high absorbency area extending from the crotch region toward the center of the front waist of the garment. It is preferred that about 65 percent of the total absorbent be in the front half of the diaper with about 40 percent of the total in the high absorbency area. The higher zones of absorbency can alternatively be formed by use of zoned superabsorbent materials.

U.S. Pat. No. 4,798,603 issued Jan. 17, 1989, to S. Meyer et al. describes an absorbent article including an absorbent body composed of a substantially hydrophilic material which is capable of absorbing a selected liquid. A liquid permeable topsheet layer composed of a substantially hydrophobic material is superposed in facing relation with an absorbent body, and has an effective average pore size therein. A liquid permeable transport layer is located between the topsheet layer and the absorbent body, and is composed of a material which is less hydrophilic than the absorbent body. The transport layer has an effective average pore size therein which is smaller than the pore size of the topsheet layer.

European Application No. 254,476 and U.S. Pat. No. 4,834,735 of Alemany et al. discloses an absorbent member having fluid storage and acquisition zones composed of cellulosic fluff mixed with absorbent gelling particles. The particles are purportedly used to keep the fibrous structure from collapsing when wet. The acquisition zone has a lower density and lower basis weight than that of the storage zone.

U.S. Pat. No. 4,673,402 to Weisman, et al. discloses a dual-layer absorbent core arrangement comprising a bottom fluff pad containing hydrogel particles, and a top fluff pad with little or no hydrogel particles.

Non-woven materials such as carded webs and spunbonded webs, have been used as the body-side liners in absorbent products. Specifically, very open, porous liner structures have been employed to allow liquid to pass through them rapidly, and help keep the body skin separated from the wetted absorbent pad underneath the liner. In addition other layers of material, such as those constructed with thick, lofty fabric structures, have been interposed between the liner and absorbent pad for the purpose of reducing wet-back.

With conventional fluff-based absorbent structures, such as those discussed above, the cellulosic fibers, when wetted, can lose resiliency and collapse. As a result, the liquid uptake rate of the wetted structures may become too low to adequately accommodate subsequent, successive liquid surges. Where absorbent gelling particles are incorporated between the fibers to hold them apart, the gelling particles swell and do not release the absorbed fluid. Swelling of the particles can then diminish the void volume of the absorbent structure and reduce the ability of the structure to rapidly uptake liquid.

The addition of more absorbent material, such as secondary fluff pledgets, or absorbent gelling particles, has been employed to increase holding capacity. The desired rate of liquid intake within such arrangements, however, may not be sufficiently sustained during successive liquid surges.

Despite the development of absorbent structures of the types surveyed above, there remains a need for improved absorbent structures which can adequately reduce the incidence of leakage from absorbent products, such as disposable diapers. There is a need for an absorbent structure which can provide improved handling of liquid surges and more effectively uptake and retain repeated loadings of liquid during use.

BRIEF DESCRIPTION OF THE INVENTION

Generally stated, the present invention provides a distinctive absorbent article comprising a backsheet layer and a topsheet layer which is disposed in facing relation with the backsheet layer. An absorbent structure is interposed between the backsheet layer and topsheet layer. The absorbent structure comprises a matrix of substantially hydrophilic fibers having a distribution of high-absorbency material therein. The hydrophilic fibers and particles of high-absorbency material are provided in a fiber-to-particle weight ratio which is not more than about 70:30, and in particular aspects of the invention, the fiber-to-particle weight ratio is not less than about 30:70. A surge management portion is located adjacent at least one major, facing surface of the topsheet layer, and the surge management portion can provide for a liquid Penetration Rate index (3rd insult) of about not less than about 2.67 ml/sec. In other aspects of the invention, the surge management portion provides for a liquid Penetration Rate index (3rd insult) of not more than about 10 ml/sec, and can provide for a Flowback index (2nd insult) of not more than about 12 gm.

The present invention can advantageously provide an absorbent article which has adequate absorptive capacity even though the bulk thickness and volume of the absorbent and article are quite small. The absorbent article can rapidly uptake body exudates, such as urine, and can maintain the rate of uptake even after the article has been previously wetted with one or more liquid insults. A surge management and control component of the invention can temporarily contain each liquid surge occurring in a target zone of the absorbent structure, and can further provide a more complete release and movement of the liquid into a retention portion of the structure. As a result, an absorbent garment article of the present invention can help avoid puddling of liquid against a wearer's skin and can more rapidly move the liquid away from the skin and into the absorbent structure. The more complete release of liquid into the retention portion of the absorbent structure helps to maintain a drier section of the article against the wearer. Thus, the distinctive structure of the present invention can reduce the amount of liquid held against the wearer's skin, reduce leakage of liquid from the absorbent article, and provide improved dryness and comfort to the wearer. In addition, the distinctive aspects of the present invention can be advantageously sustained during the course of multiple insults of liquid delivered into the absorbent structure.

BRIEF DESCRIPTION OF THE DRAWINGS

The invention will be more fully understood and further advantages will become apparent when reference is made to the following detailed description and accompanying drawings in which.

DETAILED DESCRIPTION OF THE INVENTION

The absorbent structures of the present invention will be described herein in relationship to their use in disposable absorbent articles, but it should be understood that potential uses of the absorbent structures of the present invention need not be limited to disposable absorbent articles. As used herein, the term "disposable absorbent article" refers to articles which absorb and contain body exudates and are intended to be discarded after a limited period of use. The articles are not intended to be laundered or otherwise restored for reuse. The articles can be placed against or in proximity to the body of the wearer to absorb and contain various exudates discharged From the body. While the present description will particularly be made in the context of a diaper article, it should be understood that the present invention is also applicable to other disposable personal care absorbent articles, such as adult incontinence garments, sanitary napkins, children's training pants and the like, as well as surgical bandages and sponges.

Figure 1:
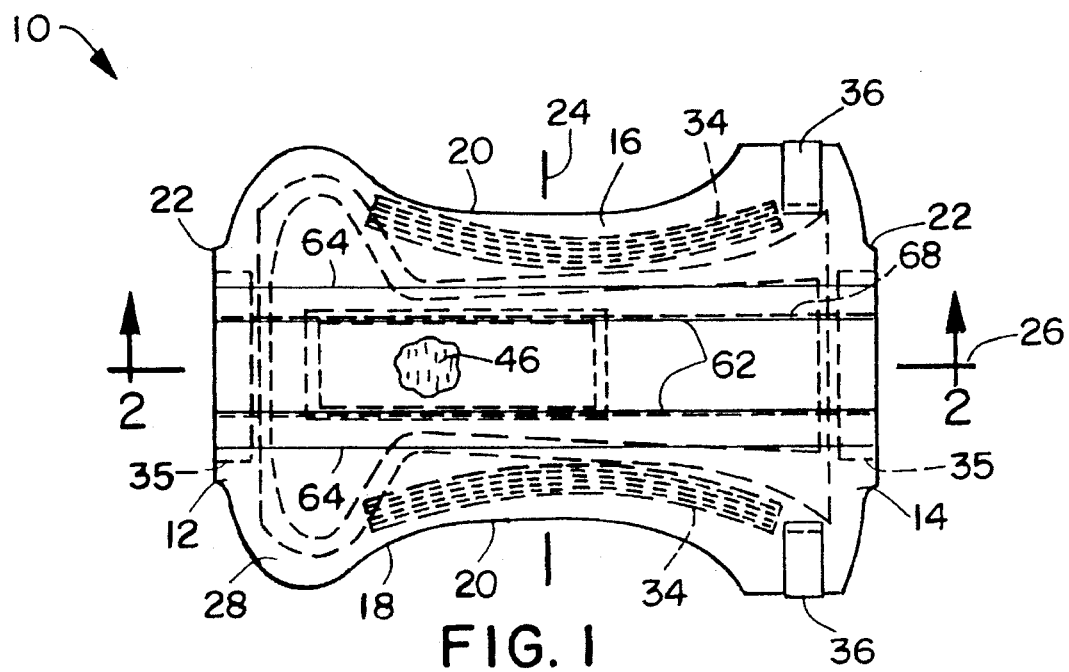
FIG. 1 representatively shows a top plan view of an embodiment of the invention, wherein the surge management portion is located between the topsheet and absorbent body, and the article has been stretched with all of the elastic gathering removed.
Figure 2:
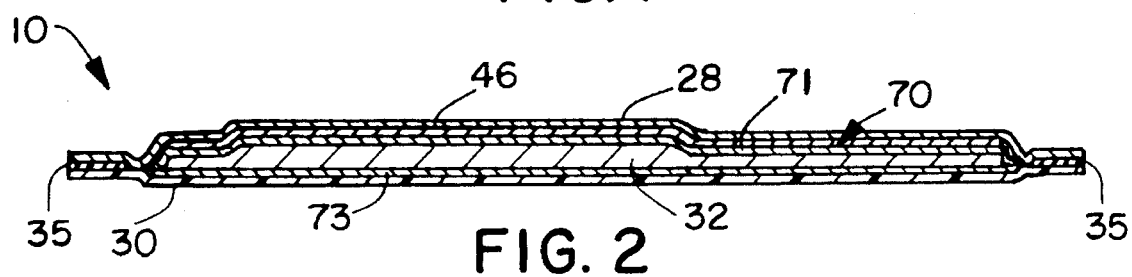
FIG. 2 representatively shows an enlarged cross-sectional view of the article of FIG. 1 taken along line 2—2, wherein particular component layers may be shown out-of-scale for the purpose of clarity.
Figure 3:
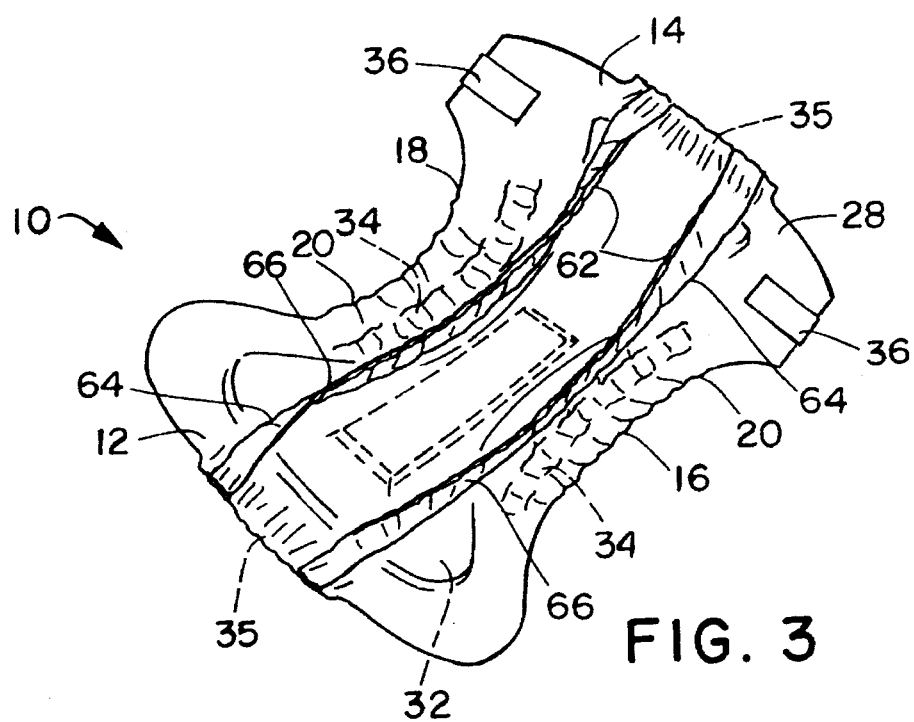
FIG. 3 representatively shows a perspective view of the article of FIG. 1, wherein the elastic members have contracted to gather the leg bands and distal edges of the containment flaps and wherein the containment flap elastics have urged the flaps to a generally upright position away from the topsheet layer.
Figure 4:
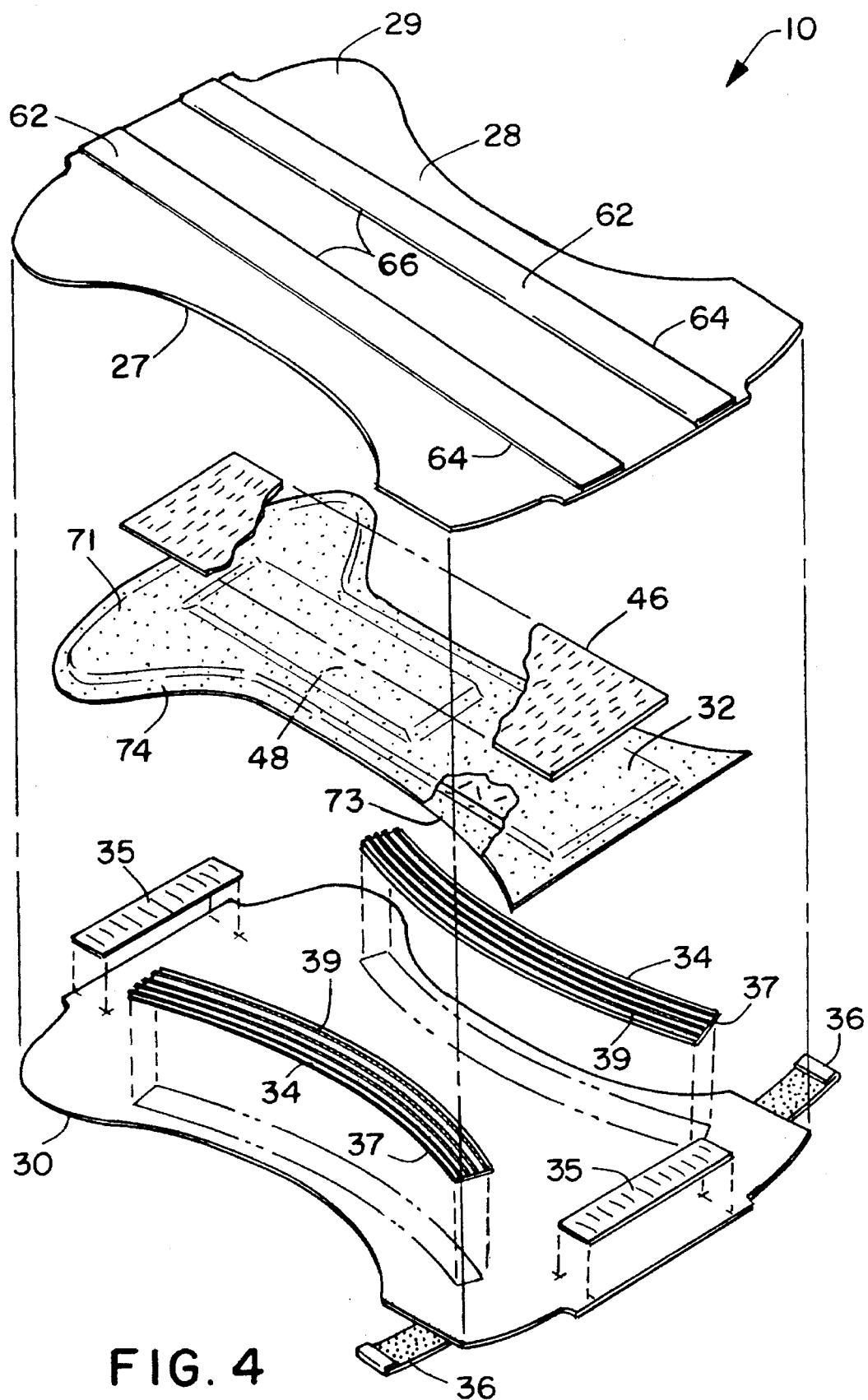
FIG. 4 representatively shows an exploded, partially cut away, perspective view of the article of FIG. 1.

Referring to FIGS. 1 and 4, an absorbent article, such as diaper 10, includes a backsheet layer 30 and a topsheet layer 28 which is disposed in facing relation with the backsheet layer. An absorbent body, such as absorbent structure 32, is interposed between backsheet layer 30 and topsheet layer 28, and includes a retention portion 48 For holding and containing body exudates, such as urine. The retention portion comprises a matrix of substantially hydrophilic fibers having therein a distribution of high-absorbency material, such as particles of superabsorbent polymer. The hydrophilic fibers and high-absorbency particles are provided in a fiber-to-particle ratio which is not more than about 70:30, and in particular constructions of the invention, the fiber-to-particle ratio is not less than about 30:70. The hydrophilic fibers and high-absorbency particles can also form an average composite basis weight which is within the range of 400–900 gsm. The absorbent structure also includes a surge management portion, such as surge layer 46, which is located adjacent at least one major, facing surface of topsheet layer 28. In addition, the surge layer provides for a liquid Penetration Rate index (third insult) of not less than about 2.67 ml/sec, particularly when assembled into the absorbent structure to cooperate with other absorbent components, such as retention portion 48. In Further aspects of the invention, the surge layer provides for a liquid Penetration Rate index of not more than about 10 ml/sec, and can advantageously provide for a Flowback index (FIFE, 2nd insult) of not more than about 12 gm.

In particular embodiments of the invention, the surge management layer can be arranged to provide a surge layer basis weight within the range of about 17–102 gsm, and can comprise nonwoven fabrics, such as spunbond webs and bonded-carded webs, composed of synthetic polymer fibers. Suitable fibers include, for example, polyester fibers, polyester/polyethylene bicomponent fibers, polypropylene/polyethylene bicomponent fibers and the like, as well as blends thereof.

In other aspects of the invention, the surge management portion can be characterized by various distinctive structural parameters. Such parameters include, for example, resiliency and bulk recovery, pore size, fiber size and surface energy.

In the illustrated embodiment, two containment flaps 62 are connected to the bodyside surface of topsheet layer 28. Suitable constructions and arrangements for containment flaps 62 are described, for example, in U.S. Pat. No. 4,704,116 issued Nov. 3, 1987, to K. Enloe, the disclosure of which is hereby incorporated by reference to the extent that it is consistent herewith.

Containment flaps 62, in the shown arrangement, are attached to topsheet layer 28 along fixed edges 64 of the flaps. A movable edge 66 of each containment flap includes a flap elastic member 68 comprising one or more individual strands of elastomeric material. For example, a plurality of elastic strands may be configured in a spatially separated, generally parallel arrangement, and a suitable elastic strand can, for example, be composed of a 470 decitex Lycra elastomer. Elastic member 68 is connected to the movable edge of the containment flap in an elastically contractible condition such that the contraction of the elastic components thereof gathers and shortens the edge of the containment flap. As a result, the movable edge of each containment flap tends to position itself in a spaced relation away from the bodyside surfaces of topsheet 28 and/or surge management portion 46 toward a generally upright and approximately perpendicular configuration, especially in the crotch section of the diaper. The containment flaps may be constructed of a material which is the same as or different than the material comprising topsheet 28. In optional embodiments, the containment flaps may be constructed of a material which is the same as or different than the material comprising surge management portion 46.

FIG. 1 is a representative plan view of diaper 10 of the present invention in its flat-out, uncontracted state (i.e., with all elastic induced gathering and contraction removed). Portions of the structure are partially cut away to more clearly show the construction of diaper 10, and the side of the diaper which contacts the wearer is facing the viewer. In the shown embodiment, diaper 10 has a front waistband region 12, a back waistband region 14, an intermediate crotch region 16 which interconnects the front and rear waistband regions. The outer edges of the diaper define a periphery 18 in which the longitudinally extending side edges are designated 20 and the laterally extending end edges are designated 22. Preferably, the side edges are curvilinear and contoured to define leg openings for the diaper. The end edges are shown as straight, but optionally, may be curvilinear. The diaper additionally has a transverse center line 24 and a longitudinal center line 26.

Diaper 10 typically includes a liquid permeable topsheet 28; a substantially liquid impermeable backsheet 30; an absorbent pad, such as absorbent structure 32, positioned between the topsheet and backsheet; and elastic members 34 and 35. Topsheet 28, backsheet 30, absorbent structure 32, and the elastic members 34 and 35 may be assembled in a variety of well-known diaper configurations. It should be recognized, however, that in articles other than diapers, individual components, such as the topsheet, backsheet or elastic members, may be optional. The desirability of including particular components in other absorbent articles would depend upon their intended end use.

In the shown embodiment of diaper 10, topsheet 28 and backsheet 30 are generally coextensive and have length and width dimensions which are generally larger than the corresponding dimensions of absorbent structure 32. Topsheet 28 is associated with and superimposed on backsheet 30, thereby defining the periphery 18 of diaper 10. The periphery delimits the outer perimeter or the edges of the diaper 10, and in the illustrated embodiment, comprises end edges 22 and contoured longitudinal edges 20. The diaper 10 has front and back waistband regions 12 and 14, respectively extending from the laterally extending end edges 22 of diaper periphery 18 toward the transverse center line 24 of the diaper along a distance of from about 2 percent to about 10 percent and preferably about 5 percent of the length of diaper 10. The waistband regions comprise those upper portions of diaper 10, which when worn, wholly or partially cover or encircle the waist or mid-lower torso of the wearer.

The intermediate, crotch region 16 lies between and interconnects waistband regions 12 and 14, and comprises that portion of diaper 10 which, when worn, is positioned between the legs of the wearer and covers the lower torso of the wearer. Thus, the crotch region 16 is an area where repeated fluid surge typically occur in diaper 10 or other disposable absorbent article.

Topsheet 28, if employed, presents a body-facing surface which is compliant, soft-feeling, and non-irritating to the wearer's skin. Further, topsheet 28 can be less hydrophilic than retention portion 48, and is sufficiently porous to be liquid permeable, permitting liquid to readily penetrate through its thickness. A suitable topsheet 28 may be manufactured from a wide selection of web materials, such as porous foams, reticulated foams, apertured plastic films, natural fibers (for example, wood or cotton fibers), synthetic Fibers (for example, polyester or polypropylene fibers), or a combination of natural and synthetic fibers. Topsheet 28 is typically employed to help isolate the wearer's skin from liquids held in absorbent structure 32.

Various woven and nonwoven fabrics can be used for topsheet 28. For example, the topsheet may be composed of a meltblown or spunbonded web of polyolefin fibers. The topsheet may also be a bonded-carded-web composed of natural and synthetic fibers.

For the purposes of the present description, the term "nonwoven web" means a web of material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 28 is a nonwoven, spunbond polypropylene fabric composed of about 2.8–3.2 denier fibers formed into a web having a basis weight of about 22 gsm and density of about 0.06 gm/cc. The fabric is surface treated with about 0.28% Triton X-102 surfactant.

Backsheet 30 may be composed of a liquid permeable material, but preferably comprises a material which is configured to be substantially impermeable to liquids. For example, a typical backsheet can be manufactured from a thin plastic film, or other flexible liquid-impermeable material. As used in the present specification, the term "flexible" refers to materials which are compliant and which will readily conform to the general shape and contours of the wearer's body. Backsheet 30 prevents the exudates contained in absorbent structure 32 from wetting articles such as bedsheets and overgarments which contact diaper 10. In particular embodiments of the invention, backsheet 30 is a polyethylene film having a thickness of from about 0.012 millimeters (0.5 mil) to about 0.051 millimeters (2.0 mils). In the shown embodiment, the backsheet is a film having a thickness of about 1.25 mil. Alternative constructions of the backsheet may comprise a woven or nonwoven fibrous web layer which has been totally or partially constructed or treated to impart the desired levels of liquid impermeability to selected regions that are adjacent or proximate the absorbent body. Backsheet 30 typically provides the outer cover of the article. Optionally, however, the article may comprise a separate outer cover member which is in addition to the backsheet.

Backsheet 30 may optionally be composed of a microporous, "breathable" material which permits vapors to escape from absorbent structure 32 while still preventing liquid exudates from passing through the backsheet. For example, the breathable backsheet may be composed of a microporous polymer film or a nonwoven fabric which has been coated or otherwise treated to impart a desired level of liquid impermeability. For example, a suitable microporous film is a PMP-1 material, which is available from Mitsui Toatsu Chemicals, Inc., a company having offices in Tokyo, Japan; or an XKO-8044 polyolefin film available from 3M Company of Minneapolis, Minn. The backsheet can also be embossed or otherwise be provided with a matte finish to exhibit a more aesthetically pleasing appearance.

The size of backsheet 30 is typically determined by the size of absorbent structure 32 and the exact diaper design selected. Backsheet 30, for example, may have a generally T-shape, a generally I-shape or a modified hourglass shape, and may extend beyond the terminal edges of absorbent structure 32 by a selected distance, such as a distance within the range of about 1.3 centimeters to 2.5 centimeters (about 0.5 to 1.0 inch).

Topsheet 28 and backsheet 30 are connected or otherwise associated together in an operable manner. As used therein, the term "associated" encompasses configurations in which topsheet 28 is directly joined to backsheet 30 by affixing topsheet 28 directly to backsheet 30, and configurations wherein topsheet 28 is joined to backsheet 30 by affixing topsheet 28 to intermediate members which in turn are affixed to backsheet 30. Topsheet 28 and backsheet 30 can be affixed directly to each other in the diaper periphery 18 by attachment means (not shown) such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix topsheet 28 to backsheet 30. The above-described attachment means may also be employed to interconnect and assemble together the other component parts of the article.

Fastening means, such as tape tab fasteners 36, are typically applied to the back waistband region 14 of diaper 10 to provide a mechanism for holding the diaper on the wearer. Tape tab fasteners 36 can be any of those well known in the art, and are typically applied to the corners of diaper 10. For example, mechanical fasteners, hook and loop fasteners, snaps, pins or buckles, may be used rather than, or in combination with adhesives and other means. It should be understood that is may be possible to dispense with the fasteners in a given design configuration.

Elastic members 34 and 35, if included in the particular article, are disposed adjacent periphery 18 of diaper 10. Along each longitudinal edge 20, leg elastic members 34 are arranged to draw and hold diaper 10 against the legs of the wearer. Waist elastic members 35 may also be disposed adjacent either or both of the end edges 22 of diaper 10 to provide elasticized waistbands. It should be noted that elasticized leg gathers and waist gathers are typically used in conventional diapers to reduce leakage caused by inadequacies of conventional absorbent structures and materials. In some instances the present invention may be advantageously configured to lessen reliance on the elasticized gathers for liquid containment purposes.

Elastic members 34 and 35 are secured to diaper 10 in an elastically contractible condition so that in a normal under strain configuration, the elastic members effectively contract against diaper 10. The elastic members can be secured in an elastically contractible condition in at least two ways, for example, the elastic members may be stretched and secured while diaper 10 is in an uncontracted condition. Alternatively, diaper 10 may be contracted, for example, by pleating, and the elastic members secured and connected to diaper 10 while the elastic members are in their unrelaxed or unstretched condition. Still other means, such as heat-shrink elastic material, may be used to gather the garment.

In the embodiment illustrated in FIG. 1, leg elastic members 34 extend essentially along the complete length of crotch region 16 of diaper 10. Alternatively, elastic members 34 may extend the entire length of diaper 10, or any other length suitable providing the arrangement of elastically contractible lines desired for the particular diaper design.

Elastic members 34 and 35 may have any of a multitude of configurations. For example, the width of the individual elastic members 34 may be varied from 0.25 millimeters (0.01 inches) to 25 millimeters (1.0 inches) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hotmelt adhesive.

Figure 11:
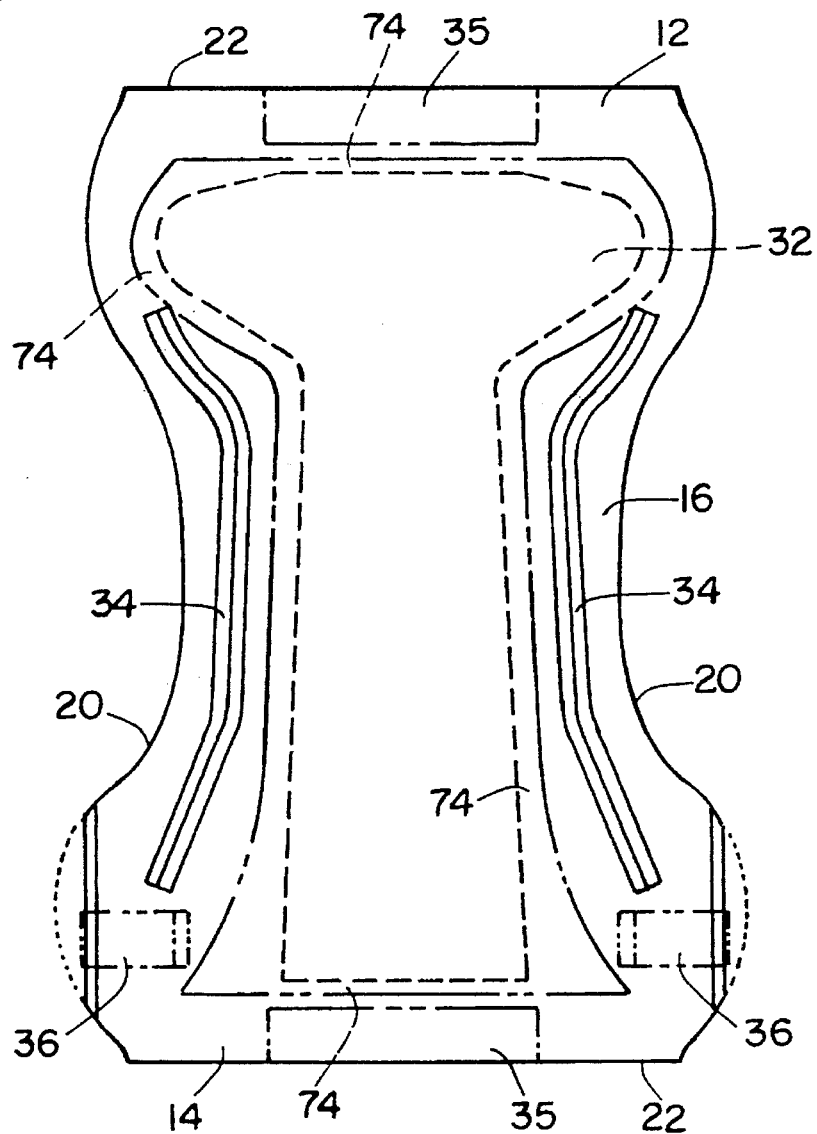
FIG. 11 representatively shows a diaper having leg elastics which are configured with a reflex curvature.

In the illustrated embodiments of the invention, leg elastic members 34 may comprise a carrier sheet 37 to which are attached a grouped set of elastics composed of a plurality of individual elastic strands 39. The elastic strands may intersect or be interconnected, or be entirely separated from each other. The shown carrier sheet may, for example, comprise a 0.002 cm thick film of unembossed polypropylene material. The shown elastic strands can, for example, be composed of Lycra elastomer available from DuPont, a business having offices in Wilmington, Del. Each elastic strand is typically within the range of about 620–1050 decitex (dtx), and preferably, is about 940 dtx in an embodiment of the invention wherein three strands are employed for each elasticized legband. In addition, leg elastics 34 may be generally straight or optionally curved. For example, the curved elastics can be inwardly bowed toward the longitudinal centerline of the diaper with the innermost point (or apex, relative to the cross-direction of the article) of the set of curved elastic strands positioned approximately 0.75–1.5 inches inward from the outer most edge of the set of elastic strands. In particular arrangements, the curvature of the elastics may not be configured or positioned symmetrically relative to the lateral centerline of the diaper. As representatively shown in FIG. 11, the curved elastics may have an inwardly bowed and outwardly bowed, reflex-type of curvature, and the length-wise center of the elastics may be offset by a selected distance within the range of about 0–8 cm toward either the front or rear waistband of the diaper to provide desired fit and appearance. In particular embodiments of the invention, the innermost point (apex) of the set of curved elastics can be offset about 0–12 cm towards the front or rear waistband of the diaper, and the outwardly bowed reflexed-portion can be positioned toward the diaper front waistband.

Due to the thinness and relatively high flexibility of the article of the invention, the leg elastics, containment flap elastics and even waist elastics, if any, should be selectively constructed and arranged to provide proper fit and adequate levels of leakage resistance. If the elastic tensions are too low or too high, the fit article of the article may be poor and there can be excessive leakage. In a particular aspect of the invention, the elastics provide for a whole article elastic tension value which is within the range of about 150–300 gm, and in a particular embodiment of the invention, the whole article tension value is about 250 gm.

Conventional methods for determining the properties of elastic systems in absorbent articles, such as disposable diapers, have required removal of the elasticized portions from the structure. Such methods eliminate the influence of other components (i.e. the absorbent core) on the elastic members. The Whole Article Elastic Tension test can advantageously determine the elastic properties of the elastic systems while the elastics are under the influence of other components of the article. The test procedure, which is set forth in detail below under TEST PROCEDURES, takes data at a specific point on the stress/strain curve, but data may also be taken at additional points on that curve to more fully characterize the product being tested.

An absorbent body, such as absorbent structure 32, is positioned between topsheet 28 and backsheet 30 to form diaper 10. The absorbent body has a construction which is generally compressible, conformable, non-irritating to the wearer's skin, and capable of absorbing and retaining liquid body exudates. It should be understood that, for purposes of this invention, the absorbent structure may comprise a single, integral piece of material, or alternatively, may comprise a plurality of individual separate pieces of material which are operably assembled together. Where the absorbent structure comprises a single, substantially integral piece of material, the material could include the desired structural features formed into selected spatial regions thereof. Where the absorbent structure comprises multiple pieces, the pieces may be configured as discrete layers or as other nonlayered shapes and configurations. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent structure. Preferably, each piece is connected to an adjacent portion of the absorbent structure by a suitable bonding and/or fiber entanglement mechanism, such as ultrasonic or adhesive bonding, or mechanical or hydraulic needling.

Figure 9:
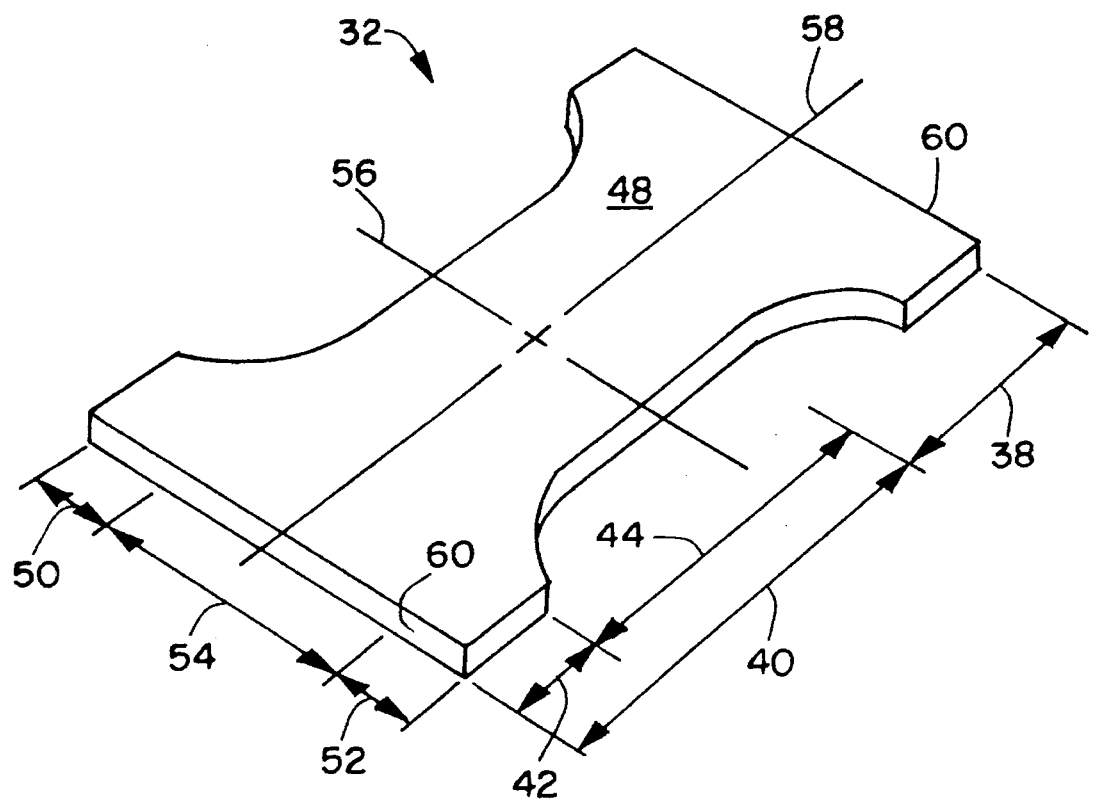
FIG. 9 representatively shows a perspective view of an exemplary absorbent structure.

In the embodiment representatively shown in FIG. 9, absorbent structure 32 includes a back section 38 and a front section 40, and the front section has an end region 42 and a target zone 44. The absorbent structure has a contoured, curvilinear periphery, particularly along its side edges. The two generally mirror-image, inwardly bowed, lateral edges provide for a narrower intermediate section suitable for positioning in the crotch of the wearer. For the purposes of the present invention, the target zone of the absorbent structure is that region of the absorbent structure which lies within a target template of the article. The width of the template is approximately 13% of the sum of the front and rear, laterally extending, waistband edges 22 of the outer cover of the article. The length of the template is approximately 45% of the overall length of the article's outer cover. The template is centered over the longitudinal, length-wise centerline of the article, and one laterally extending (i.e. width-wise) edge of the template is positioned about 1.3 cm inward from the front waistband edge of the absorbent structure. The opposite, laterally extending edge of the template positioned toward the rear waistband edge of the article. The section of the absorbent structure which then lies within the area of the template is the target zone of the absorbent structure.

The absorbent structure additionally has a transverse center line 56 and a longitudinal center line 58. The absorbent structure may be configured with a part of retention portion 48 located within target zone 44 and the remainder of retention portion 48 located outside of the target zone. In an alternative arrangement, none of the retention portion is positioned within target zone 44, and the retention portion is totally located outside of the target zone. In yet another arrangement, all of retention portion 48 may be positioned within target zone 44.

In absorbent structure 32, front section 40 can be conceptually divided into three regions comprising two transversely spaced ear regions 50 and 52 respectively, and a central region 54. Front section 40 is contiguous with back section 38, and the back and front sections of absorbent structure 32 extend away from the end edges 60 of absorbent structure 32 toward transverse center line 56. The relative dimensions of the various sections and portions of diaper 10, and of absorbent structure 32, can be varied depending on materials used and the desired product needs. For example, front portion 40 can extend over a distance corresponding to about one-half to two-thirds, or even three-fourths of the length of absorbent structure 32. Front section 40 is constructed to encompass all of the fluid target zone 44 of absorbent structure 32 within the diaper or other absorbent article.

The front portion 40 includes an end region 42 and at least a portion of target zone 44. End region 42 comprises the portion of front section 40 extending a selected distance from the respective end edge 60 of absorbent structure 32 toward transverse center line 56. Target zone 44 is contiguous with end region 42 and back section 38, and encompasses the area where repeated liquid surges typically occur in absorbent structure 32. The particular location where liquid is discharged, such as during micturition, varies depending on the age and gender of the wearer. For example, male infants tend to urinate further toward the front end of the diaper. The female target zone is located closer to the center of the crotch. As a result, the shape and relative longitudinal placement of surge management portion 46 can be selected to best correspond with the actual target zone of either or both categories of wearers. Generally stated, the target zone is a section of absorbent structure 32 which is located in the front 60% of the length of absorbent structure. With reference to the percentage of the total length of absorbent structure 32 measured into absorbent structure from the front waistband edge thereof, the target zone may preferably comprise a region which begins at a line positioned approximately 10% of the absorbent structure length away from the front waistband edge and ends at approximately 60% of the absorbent structure length away from the front waistband edge.

The ear regions 50 and 52 comprise portions which generally extend from the lateral side edges of the absorbent structure toward longitudinal center line 58 a distance from one-tenth to one-third of the overall width of absorbent structure 32, and connect to central region 54. Thus, when the diaper is worn, the ear regions are configured to generally engage the sides of the wearer's waist and torso, and central region 54 is configured to generally engage the medial portion of the wearer's waist and torso.

Absorbent structure 32 may be manufactured in a wide variety of sizes and shapes (for example, rectangular, trapezoidal, T-shape, I-shape, hourglass shape, etc.) and from a wide variety of materials. The size and the absorbent capacity of absorbent structure 32 should be compatible with the size of the intended wearer and the liquid loading imparted by the intended use of the absorbent article. Further, the size and the absorbent capacity of absorbent structure 32 can be varied to accommodate wearers ranging from infants through adults. In addition, it has been found that with the present invention, the densities and/or basis weights of the respective surge management 46 and retention 48 portions, as well as their relative ratios, can be varied.

In a particular aspect of the invention, the absorbent structure has an absorbent capacity of at least about 300 gm of synthetic urine. Preferably, the absorbent structure has an absorbent capacity of at least about 400 gm of synthetic urine to provide improved performance.

Various types of wettable, hydrophilic fibrous material can be used to form the component parts of absorbent structure 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, For example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials used for the surge management portion 46 can be provided by a Cahn SFA-222 Surface Force Analyzer System. When measured with this system in accordance with the procedure described in detail herein below, fibers having contact angles less than 90° are designated "wettable", while fibers having contact angles greater than 90° are designated "nonwettable"

As representatively shown in FIGS. 4, retention portion 48 can be situated in target zone 44, and can substantially define the boundaries of absorbent structure 32. Retention portion 48 can comprise a matrix of hydrophilic fibers, such as a web of cellulosic fluff, mixed with particles of high-absorbency material. In particular arrangements, retention portion 48 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent structure and relatively higher concentrations toward the outside of the absorbent structure. Suitable z-gradient configurations are described in U.S. Pat. No. 4,699,823 issued Oct. 13, 1987 to Kellenberger et al., the disclosure of which is incorporated herein by reference to the extent that it is consistent with the present description. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly(acrylic acid) and poly (methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarson et al. in U.S. Pat. No. 3,902,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto eta.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in retention portion 48 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in retention portion 48.

Preferred for use are particles having an average size of from about 20 microns to about 1 millimeter. "Particle size" as used herein means the weighted average of the smallest dimension of the individual particles.

In particular aspects of this invention, the superabsorbent particles exhibit a Deformation Under Load which is about 0.6 millimeter or less, preferably is about 0.4 millimeter or less, and more preferably is about 0.3 millimeter or less. A suitable range for the Deformation Under Load is from about 0.3 to about 0.6 millimeter.

In another aspect of the invention, the superabsorbent material exhibits a Wicking Index which is about 10 centimeters or greater, preferably is about 12 cm or greater, more preferably is about 15 cm or greater and most preferably is about 18 cm or greater. A suitable range for the Wicking Index is from about 12 to about 19.

In a further aspect of the invention, the superabsorbent material exhibits an Absorbent Capacity which is preferably about 29 grams per gram or greater, more preferably is about 32 gm/gm or greater, still more preferably is about 36 gm/gm or greater, and most preferably about 40 gm/gm or greater. A suitable Absorbent Capacity range is from about 29 to about 41 gm/gm.

In one embodiment of the invention, for example, the superabsorbent material has a Deformation Under Load of about 0.60 millimeter or less, and has a Wicking Index of about 10 centimeters or greater. An Absorbent Capacity of about 28 grams per gram or greater is preferred.

Suitable methods for determining Absorbent Capacity (sometimes referred to as "AC"), Deformation Under Load (sometimes referred to as "DUL"), and the Wicking Index (sometimes referred to as "WI") are described in detail in U.S. patent application Ser. No. 07/757,787 of S. Byerly et al. and entitled "ABSORBENT COMPOSITES AND ABSORBENT ARTICLES CONTAINING SAME" (Attorney Docket No. 0174), which was filed on even date herewith and is hereby incorporated by reference to the extent that it is consistent with the present specification.

In a particular aspect of the invention, absorbent retention portion 48 comprises a matrix of substantially hydrophilic fibers having a quantity of high-absorbency material distributed therein. Selected superabsorbent polymers having improved absorbent properties can be important for maximizing the performance while retaining the desired thinness of the absorbent article. To provide improved performance, the particles of superabsorbent material can be selected to provide an absorbency-under-load (AUL) value which is within the range of about 25–40, and provide a Absorbent Capacity (AC) value which is within the range of about 32–48. The rate of liquid uptake by the superabsorbent material is within the range of about 3–15 g/g (grams liquid per gram superabsorbent) at 30 seconds of absorbency under load, 6.5–21 g/g at 5 minutes absorbency under load and 25–40 g/g at 60 minutes absorbency under load.

A suitable method for determining AUL is described in detail in U.S. patent application Ser. No. 184,302 of S. Kellenberger and entitled "Absorbent Products Containing Hydrogels with Ability to Swell Against Pressure" (Attorney Docket No. 8786); European Patent Application EP 0 339 461A1, published Nov. 2, 1989; the disclosure of which is hereby incorporated by reference to the extent that it is consistent with the present specification.

An example of superabsorbent polymer suitable for use in the present invention is SANWET IM 3900 polymer available from Hoechst Celanese, a business having offices in Portsmouth, Va. Other suitable superabsorbents may include W45926 polymer obtained from Stockhausen, a business having offices in Greensboro, N.C.

The matrix of hydrophilic fibers comprising retention portion 48 may be a layer of cellulosic wood pulp fluff, and the particles of superabsorbent polymer can be distributed within the matrix of hydrophilic fibers. The hydrophilic fibers and high-absorbency particles are provided in a fiber-to-particle ratio which is not more than about 70:30, preferably is not more than about 60:40 and more preferably is not more than about 55:45, by weight. In further aspects of the invention, the fiber-to-particle ratio is not less than about 30:70, preferably is not less than about 40:60 and more preferably is not less than about 45:55, by weight. Such fiber-to-particle ratios can be particularly desireable in the target zone of the absorbent structure. In particular embodiments of the invention, the fiber-to-particle weight ratio is not more than about 52:48 and is not less than about 48:52 to provide desired performance.

The hydrophilic fibers and high-absorbency particles form an average composite basis weight which is within the range of about 400–900 gsm. Again, such basis weight is particularly desireable in the target zone of the absorbent structure. In certain aspects of the invention, the average composite basis weight is within the range of about 500–800 gsm, and preferably is within the range of about 550–750 gsm to provide desired performance.

To provide the desired thinness dimension to the absorbent article, retention portion 48 is configured with a bulk thickness which is not more than about 0.6 cm. Preferably, the bulk thickness is not more than about 0.53 cm, and more preferably is not more than about 0.5 cm to provide improved benefits. The bulk thickness is determined under a restraining pressure of 0.2 psi (1.38 kPa).

The density of retention portion 48 or other component of the absorbent article can be calculated from its basis weight and thickness. With respect to diapers, for example, the weight and thickness are measured on newly unpacked, unfolded and dry diapers at a restraining pressure of 0.2 psi (1.38 kPa). For measuring bulk thickness to calculate densities, a suitable device is a TMI foam thickness gauge, Model No. TM1-49-21 or its equivalent. The apparatus is available from Testing Machines, Inc. of Amityville, N.Y.

In some liquid retention structures comprising mixtures of hydrophilic fiber and gelling material, attempts to ameliorate gel blocking have employed a densification of such absorbent structures to ostensibly enhance the liquid wicking rate along the general plane of the structure (X-Y direction) as a result of a higher capillary force created by the smaller pore sizes within the matrix of densified fibers. Although densifying the absorbent structure does reduce the bulk thickness of the structure, the higher density may excessively reduce the rate of liquid intake.

In particular, the densification of retention portion 48 can reduce the rate of liquid movement into retention portion 48 along the thickness dimension; i.e., the Z-direction which is normal to the general X-Y plane of the article. It is believed that as higher concentrations of absorbent gelling material are located in the area of desorption underneath surge management portion 46, a greater gel blocking effect may be created, thereby reducing the liquid intake rate. Accordingly, the materials in target zone 44 may optionally incorporate reduced amounts of absorbent gelling material or a different type of gelling material having a reduced or delayed uptake rate, thereby helping to reduce the incidence of gel-blocking in this zone and improve the liquid intake rate.

In the illustrated embodiments of the invention, absorbent retention portion 48 includes 5–22 grams of wood pulp fluff, preferably includes about 8–14 grams of fluff and more preferably includes about 10–12 grams of fluff to provide desired benefits. The wood pulp fluff generally provides shape and form to diaper 10, and carries and positions the particles of superabsorbent polymer or other high-absorbency material. Retention portion 48 can contain about 8–12 grams of superabsorbent polymer, and in the shown embodiment, contains about 10 grams of superabsorbent polymer. Sufficient superabsorbent polymer is incorporated into retention portion 48 to provide an adequate total absorbent capacity of at least about 300 gm of urine. For example, a medium size diaper for an infant weighing about 13–23 lb can typically have a total retention capacity of about 500 grams of urine.

The fluff and superabsorbent particles can be selectively placed into desired zones of retention portion 48. For example, the fluff basis weight may vary across the width dimension of retention portion 48. Alternatively, relatively larger amounts of fluff may be positioned toward the front waistband end of the retention portion. For example, see U.S. Pat. No. 4,585,448 issued Apr. 29, 1986, to K. Enloe. In the illustrated embodiment, the majority of the superabsorbent material is distributed down a medial region of retention portion 48 which extends along the length dimension of the retention portion and measures about 3.5–4.5 inches in width. In addition, the superabsorbent material may have a selected zoned placement to reduce the amount of superabsorbent material located proximate the side and end edges of the retention portion. The reduced amounts of superabsorbent material at the edges of the retention portion can improve the containment of the superabsorbent particles within the fibrous fluff matrix of retention portion 48. The pulsed, zoned placement of the superabsorbent material can, for example, be achieved by the method and apparatus described in copending U.S. patent application Ser. No. 07/462,363 of C. Pieper et al. filed Jan. 9, 1990, and entitled "Method and Apparatus for Intermittently Depositing Particulate Material in a Substrate" (Attorney Docket No. 8761), the disclosure of which is hereby incorporated by reference to the extent that it is consistent herewith.

In a particular aspect of the invention, absorbent structure 32 is generally T-shaped with the laterally extending crossbar of the "T" generally corresponding to the front waistband portion of the absorbent article for improved performance, especially for male infants. In the illustrated embodiments, the retention portion across the ear section of the front waistband region of the article has a cross-directional width of about 9.0 inches, the narrowest portion of the crotch section has a width of about 3.5 inches and the back waistband region has a width of about 4.5 inches.

Figure 10:
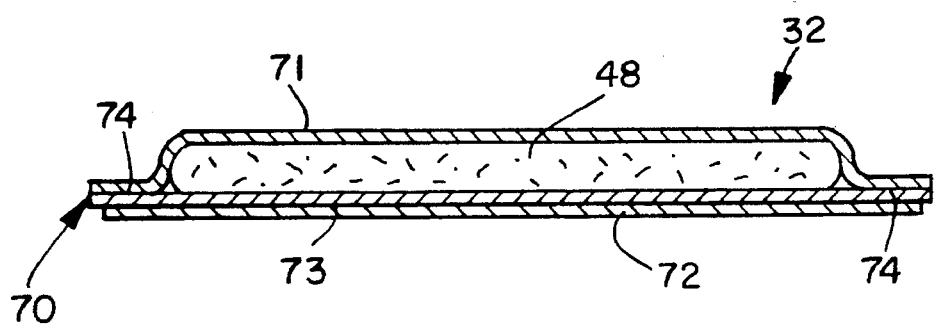
FIG. 10 representatively shows a cross-sectional view of a multicomponent absorbent wrapsheet.

With reference to FIG. 10, the entire absorbent structure 32, or any individual portion thereof, such as the retention portion, can be overwrapped in a hydrophilic high wet-strength envelope web, such as a high wet-strength tissue or a synthetic fibrous web. Such overwrapping web can also increase the in-use integrity of the absorbent structure. The web can be suitably bonded, such as with adhesive, to absorbent structure 32 and to other components of the product construction.

Due to the high concentrations of superabsorbent particles, or other high-absorbency material, in retention portion 48, there can be an increased difficulty with regard to containing the high-absorbency particles within the retention portion and restricting the movement or migration of the superabsorbent onto the bodyside of the diaper. To improve the containment of the high-absorbency material, absorbent structure 32 can include an improved overwrap, such as wrap sheet 70, placed immediately adjacent and around retention portion 48. The wrap sheet is preferably a layer of absorbent material which covers the major bodyside and outerside surfaces of the retention portion, and preferably encloses substantially all of the peripheral edges of the retention portion to form a substantially complete envelope thereabout. Alternatively, the wrap sheet can provide an absorbent wrap which covers the major bodyside and outerside surfaces of the retention portion, and encloses substantially only the lateral side edges of the retention portion. Accordingly, both the linear and the inwardly curved portions of the lateral side edges of the wrap sheet would be closed about the retention portion. In such an arrangement, however, the end edges of the wrap sheet may not be completely closed around the end edges of the retention portion at the waistband regions of the article.

At least the bodyside layer of wrap sheet 70 has a pore distribution wherein no more than about 5 percent of the pores, as measured by Coulter porometry, are greater than about 50 micrometers in diameter. For example, the complete wrap sheet 70, or at least the bodyside layer of the wrap sheet, may comprise a meltblown web composed of meltblown polypropylene fibers having a fiber size of about 5 micrometers and arranged to form a basis weight within the range of about 8–20 gsm.

Another example of absorbent wrap 70 may comprise a low porosity cellulosic tissue web composed of an approximately 50/50 blend of hardwood/softwood fibers. The tissue has a 13 lb basis weight at the reel and a porosity of about 90 cfs/sq. ft. Similar to the meltblown wrap sheet material, the entire tissue wrapsheet material, or at least the bodyside layer thereof, has not more than about 5 percent of its pores greater than about 50 micrometers in diameter. Preferably, not more than about 1 percent of the pores are greater than 50 micrometers in diameter.

Absorbent wrap 70 may comprise a multi-element wrapsheet which includes a separate bodyside wrap layer 71 and a separate outside wrap layer 73, each of which extends past all or some of the peripheral edges of retention portion 48, as representatively shown in FIG. 10. Such a configuration of the wrap sheet can, for example, facilitate the formation of a substantially complete sealing and closure around the peripheral edges of retention portion 48. In the back waistband portion of the illustrated diaper, the absorbent wrap may also be configured to extend an increased distance away from the periphery of the retention portion to add opacity and strength to the back ear sections of the diaper. In the illustrated embodiment, the bodyside and outerside layers of absorbent wrap 70 extend at least about ½ inch beyond the peripheral edges of the retention portion to provide an outwardly protruding, flange-type bonding area 74 over which the periphery of the bodyside portion of the absorbent wrap may be completely or partially connected to the periphery of the outerside portion of the absorbent wrap.

The bodyside and outerside layers of wrap sheet 70 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

To provide the bonding between the bodyside and outerside portions of absorbent wrap 70, an adhesive, such as National Starch 72-3723 adhesive, can be printed onto the appointed bonding areas 74 of the absorbent wrap with, for example, a rotogravure-type system. The adhesive is available from National Starch and Chemical Co., a business having offices in Bridgewater, N.J., and rotogravure-type adhesive applicators are available from Egan Machinery Division, a business having offices at Oconto Falls, Wis. Retention portion 48 can then be placed between the bodyside and outerside portions of absorbent wrap 70 and the mating edges of the absorbent wrap portions can be bonded together to provide a generally complete peripheral seal along substantially the entire perimeter of retention portion 48. In the illustrated embodiment, the adhesive is applied at an add-on rate of about 5 grams of solids per square meter of bonding to attach together the lapping edges of the bodyside and outerside portions of absorbent wrap 70.

With alternative arrangements having an absorbent wrap composed of a nonwoven meltblown fibrous web, the peripheral sealing of the bodyside and outerside wrap layers may be accomplished by employing hot calendering to provide a sealed strip region around the periphery of the retention portion. For example, absorbent wrap 70 may comprise a first nonwoven layer of meltblown fibers positioned adjacent the bodyside of retention portion 48, and a second meltblown fibrous layer positioned adjacent an outerside of the retention portion. The contacting portions of the first and second meltblown fabrics are thermally bonded around the periphery of the retention portion employing an intermittent, discontinuous thermal bonding pattern, such as a shaped-dot pattern. Such a bonding pattern can provide a labyrinth-type seal which can more effectively inhibit undesired movements of the high-absorbency particles without excessively stiffening the bonded area. The thermal bonding process can employ an unheated anvil roll and a heated pattern roll, which is heated to a temperature of about 250° C. The resultant thermal bonding may be accomplished at speeds of up to 990 feet/second.

Due to the thinness of retention portion 48 and the high superabsorbent concentrations within the retention portion, the liquid uptake rates of the retention portion, by itself, may be too low, or may not be adequately sustained over three insults of liquid into the absorbent structure. The addition of a layer of surge management material, however, can advantageously improve the overall uptake rate of the composite absorbent structure. Surge management portion 46 is typically less hydrophilic than retention portion 48, and has an operable level of density and basis weight to quickly collect and temporarily hold liquid surges, and to transport the liquid from its initial entrance point to other parts of the absorbent structure 32, particularly retention portion 48. This configuration can help prevent the liquid from pooling and collecting on the portion of the absorbent garment positioned against the wearer's skin, thereby reducing the feeling of wetness by the wearer.

Various woven and nonwoven fabrics can be used to construct surge management portion 46. For example, the surge management portion may be a layer composed of a meltblown or spunbonded web of polyolefin fibers. The surge management layer may also be a bonded-carded-web composed of natural and synthetic fibers. The surge management portion may be composed of a substantially hydrophobic material, and the hydrophobic material may optionally be treated with a surfactant or otherwise processed to impart a desired level of wettability and hydrophilicity.

In addition, the surge management layer can be configured with an average bulk density which is not more than about 0.10 g/cc (determined at 0.2 psi). Preferably, the bulk density of the surge management layer is within the range of about 0.02–0.06 g/cc to provide improved effectiveness. The types of nonwoven materials that may be employed include powder-bonded-carded webs, infrared bonded carded webs, and through-air-bonded-carded webs. The infrared and through-air bonded carded webs can optionally include a mixture of different fibers, and the fiber lengths within a selected fabric web may be within the range of about 1.0–3.0 inch.

Surge management portion 46 preferably has a generally uniform thickness and cross-sectional area. Alternatively, a configuration can be used wherein the bodyside surface area of the surge management portion is greater or less than the surface area of a section taken along an X-Y plane located below the bodyside surface of the surge management portion.

Figure 5:
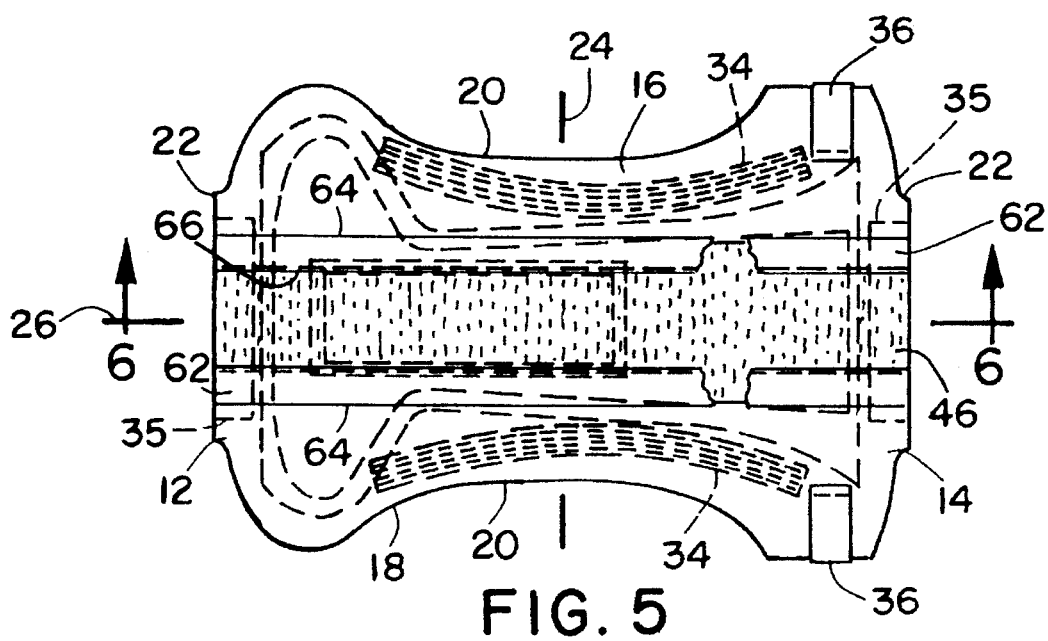
FIG. 5 representatively shows a top plan view of another embodiment of the invention, wherein the surge management portion is positioned on the bodyside surface of the topsheet, and the article has been stretched with all of the elastic gathering removed.
Figure 6:
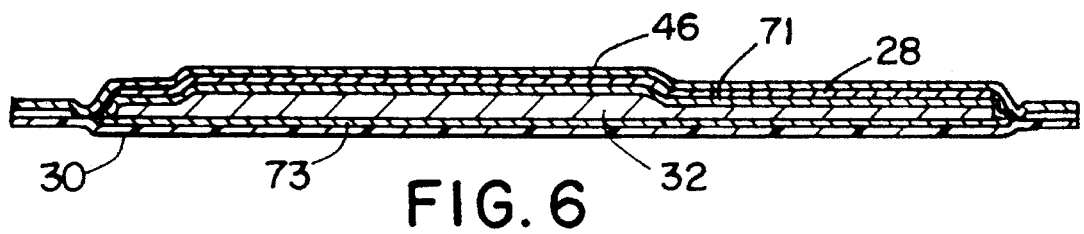
FIG. 6 representatively shows an enlarged, cross-sectional view of the article of FIG. 5 taken along line 6—6, wherein particular component layers may be shown out-of-scale for the purpose of clarity.
Figure 7:
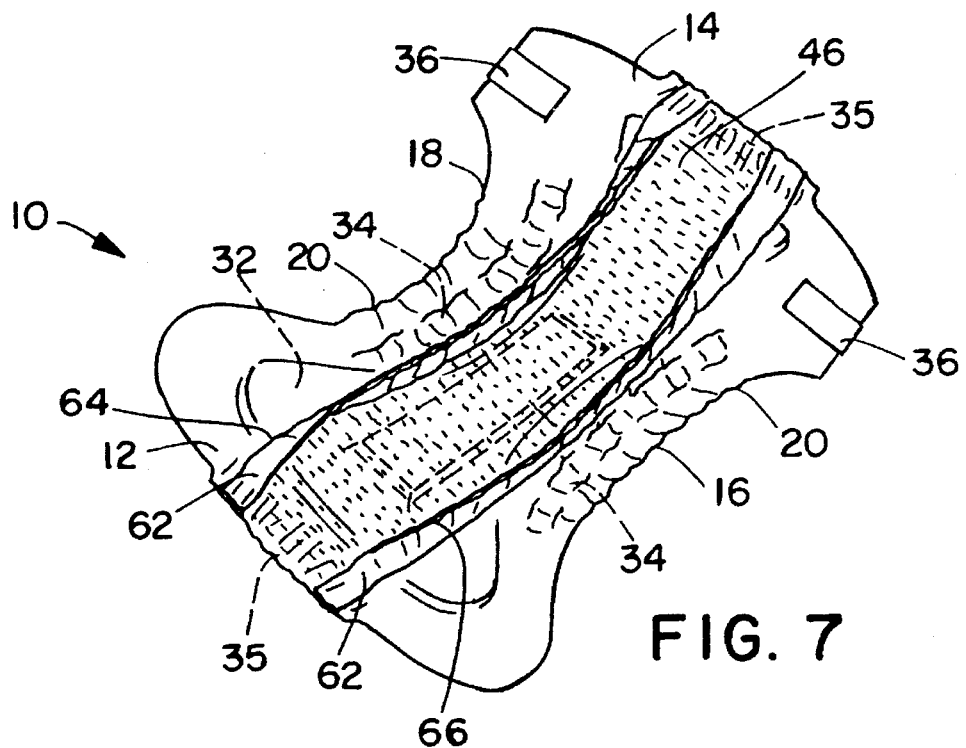
FIG. 7 representatively shows a perspective view of the article of FIG. 5, wherein the elastic members have contracted to gather the leg bands and distal edges of the containment flaps and wherein the containment flap elastics have urged the flaps to a generally upright position away from the topsheet layer.

With reference again to FIG. 1, the absorbent article represented by diaper 10 can generally comprise a liquid surge management portion 46 and an absorbent retention portion 48 adjacently arranged in direct, contacting liquid communication with the surge management portion. As representatively shown in FIGS. 5 and 8, surge management portion 46 may be alternatively be configured for placement adjacent an inwardly facing, bodyside of topsheet 28.

In the various embodiments of the invention, at least a part of surge management portion 46 is located within target zone 44, and preferably, the surge management portion has an areal extent which extends completely over target zone 44. Retention portion 48 is positioned in liquid communication with surge management portion 46 to receive liquids released from the surge management portion, and to hold and store the liquid. In the shown embodiments, surge management portion 46 comprises a separate layer which is positioned over another, separate layer comprising the retention portion, thereby forming a dual-layer arrangement. The surge management portion serves to quickly collect and temporarily hold discharged liquids, to transport such liquids from the point of initial contact and spread the liquid to other parts of the surge management portion, and then to eventually release such liquids into the layer or layers comprising retention portion 48.

The layer comprising the surge management portion is substantially free of absorbent gelling material. Surge management portion 46 may, however, contain a very small amount of particulate gelling material to help acquire an initial liquid surge, but the amount should not be excessive. When excessive amounts of particulate absorbent gelling material are maintained in target zone 44, however, the particles can cause the structure to retain and hold unacceptably high amounts of the liquid. In addition, the transport of liquids away from target zone 44 to other sections of absorbent structure 32, particularly retention portion 48, can be undesirably impaired.

As mentioned previously, surge layer 46 can be a separately formed layer, which lies adjacent the outerwardly facing surface of topsheet 28 between the retention portion and topsheet. Thus, surge management portion 46 need not comprise the entire thickness of absorbent structure 32. The retention portion can optionally include a recess area which wholly or partially surrounds surge management portion 46, or the retention portion can be entirely positioned below the surge management portion. The arrangement which includes the recess in retention portion 48 can advantageously increase the area of contact and liquid communication between the retention portion and surge management portion 48. It should be understood, however, that surge management portion 46 could optionally be constructed to extend through the entire thickness of absorbent structure 32 so that the capillary flow of liquid into retention portion 48 occurs primarily in the generally sideways (X-Y) direction.

A capillary force differential created at the interface between the retention portion 48 and the material immediately adjacent the bodyside of the retention portion can improve the containment characteristics of absorbent structure 32. For example, if the surge management portion is composed of layer 46 positioned immediately adjacent to the retention portion, and if the surge layer is appropriately configured to provide and maintain a relatively lower capillary attraction, as compared to the capillary attraction exhibited by retention portion 48, then liquid surges occurring in target zone 44 tend to be desorbed more readily from the surge management portion and into the retention portion. Because retention portion 48 can thereby have a relatively higher capillarity than surge management portion 46, the liquid surges tend to be drawn into retention portion 48 and distributed to the more remote regions thereof by wicking along the plane generally defined by the retention portion.

The surge management portion can be of any desired shape consistent with the absorbency requirements of absorbent structure 32. Suitable shapes include for example, circular, rectangular, triangular, trapezoidal, oblong, dog-boned, hourglass-shaped, or oval. Preferred shapes of the surge management portion are those that increase the contacting, liquid communicating surface area between surge management portion 46 and retention portion 48 so that the relative capillarity difference between the portions can be fully utilized. In certain embodiments, such as shown in FIGS. 3–6 and 8–9, the surge management portion can be generally rectangular-shaped with a top surface area within the range of about 15–102 in$^2$(about 97–660 cm$^2$). In the shown embodiment, surge layer 46 has a top surface area of about 45 square inches (about 290 cm$^2$).

In the various embodiments of the invention, such as the arrangement of FIG. 1 where surge management portion 46 is interposed between topsheet 28 and retention portion 48, the surge management portion can comprise a nonwoven fabric which has a basis weight within the range of about 17–102 gsm and includes at least about 25 wt % of bicomponent fibers to provide a desired bicomponent fiber bond-matrix. Up to 100% of the surge fabric can be composed of bicomponent fibers, and accordingly, 0–75 wt % of the fabric may comprise non-bicomponent fibers. In addition, the fabric can comprise a blend of smaller diameter fibers and relatively larger diameter fibers. The smaller sized fibers have a denier of not more than about 3 d, and preferably have a denier within the range of about 0.9–3 d. The larger sized fibers have a denier of not less than about 3 d, and preferably have a denier within the range of about 3–18 d. The lengths of the fibers employed in the surge management materials are within the range of about 1–3 in. The bond-matrix and the blend of fiber deniers can advantageously provide for and substantially maintain a desired pore size structure.

For example, the surge management portion may comprise a nonwoven fibrous web which includes about 75 percent polyester fibers of at least 6 denier, such as PET (polyethylene terephthalate) fibers available from Hoechst Celanese. The polyester fibers have a length ranging from about 1.5–2.0 inches in length. The remaining 25 percent of the fibrous web can be composed of bicomponent binder fibers of not more than 3 denier, and preferably about 1.5 denier. The bicomponent fiber length ranges from about 1.5–2 inches. Suitable bicomponent fibers are a wettable, polyethylene/polypropylene bicomponent fiber, available from Chisso, a business having offices located in Osaka, Japan. The bicomponent fiber can be a composite, sheath-core type with the polypropylene forming the core and polyethylene forming the sheath of the composite fiber. The polyester fibers and bicomponent fibers are generally homogeneously blended together and are not in a layered configuration. The fibers can be formed into a carded web which is thermally bonded, such as by through-air bonding or infrared bonding.

As another example, the surge management portion may be composed of a bonded carded web which has a basis weight of about 50 gsm and includes a mixture of polyester (PET) single-component fibers and PET/polyethylene bicomponent fibers. The PET fibers comprise about 60 wt % of the nonwoven fabric, and are about 6 denier with an average fiber length of about 2 in. The PET/polyethylene bicomponent fibers comprise about 40 wt % of the fabric, and are about 1.8 denier with an average fiber length of about 1.5 in. The PET forms the core and the polyethylene forms the sheath of the fiber. In optional constructions, the larger-sized, PET single-component fibers may be replaced by bicomponent fibers. In further optional arrangements, polypropylene/polyethylene bicomponent fibers may be employed to form the bicomponent fiber portion of any of the described fabrics. In addition, the bicomponent fibers may be flat crimped or helically crimped.

Figure 12:
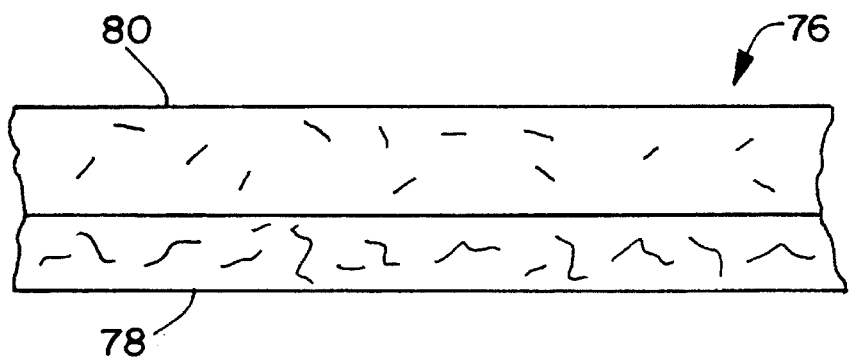
FIG. 12 representatively shows a cross-sectional view of a multilayer, composite surge management material.

Referring again to FIG. 5, surge management portion 46 can be advantageously configured for placement against the bodyside of topsheet 28. Accordingly, an outward major surface of the surge management portion would be immediately adjacent and contact the topsheet, and the opposite, innerward major surface of the surge management portion would contact the skin of the wearer. In the shown embodiment, backsheet 30 defines a front waistband section 12, a rear waistband section 14, and an intermediate or crotch section 16 interconnecting the front and rear waistband sections. The backsheet has predetermined width and length dimensions, and an absorbent body 32 is superposed on the backsheet. Topsheet layer 28 is disposed in facing relation with said absorbent body to generally sandwich said absorbent body between said backsheet and topsheet layers, and the topsheet has an appointed outside surface 27 and an appointed bodyside surface 29. A width dimension of topsheet 28 is configured to extend completely over the width of the absorbent body in at least a portion of the crotch section of the absorbent body. With the shown embodiment, the topsheet is also substantially coextensive with the backsheet width over at least a portion of the backsheet crotch section. A surge management portion, such as surge layer 46, is located on the bodyside surface of the topsheet layer, with the surge layer having a width dimension which is less than the width of said topsheet layer.

Where surge management portion 46 is configured for placement adjacent the bodyside of topsheet 28, the surge management portion can be a composite, liner-surge web 76. The composite web includes a bodyside layer portion 80 and an outerside layer portion 78, as representatively shown in FIG. 12. The layer portions can be separately laid and can have different structures and compositions. The fibers within each layer and the intermingling fibers between the layer portions are then suitably interconnected (such as by powder bonding, point bonding, adhesive bonding, atex bonding, or by through-air or infrared thermal bonding) to form a composite web. The resultant composite web has a total basis weight of not more than about 102 gsm. Preferably the total basis weight is within the range of about 24–68 gsm, and more preferably is within the range of about 45–55 gsm. In addition, the total average density of the composite web is not more than about 0.10 g/cc, and preferably is not more than about 0.05 g/cc (as determined at 0.2 psi).

Outerside, surge layer 78 has a basis weight within the range of about 17–50 gsm and includes at least about 25 wt % of bicomponent fibers to provide a desired bicomponent fiber bond-matrix. The outerside layer also comprises a blend of smaller diameter fibers and relatively larger diameter fibers. The smaller sized fibers have a denier within the range of about 0.9–3 d, and the larger sized fibers have a denier within the range of about 3–15 d. The bond-matrix and the blend of fiber deniers can advantageously provide for and substantially maintain a desired pore size structure within outerside layer 78.

For example, the outerside layer may be composed of a carded web which has a basis weight of about 34 gsm and includes a mixture of polyester (PET) single-component fibers, available from Hoechst-Celanese, and polyethylene/PET (PE/PET) sheath-core bicomponent fibers, available from BASF Corp., Fibers Division, a business having offices in Enka, N.C. The PET fibers can comprise about 60 wt % of the outerside layer and have a denier of about 6 with an average fiber length of about 2 in. The polyethylene/PET bicomponent fibers comprise about 40 wt % of the outerside layer, and have a denier of about 1.8 with an average fiber length of about 1.5 in. Optionally, the larger-sized, PET single-component fibers may be replaced by bicomponent fibers. As a further option, polyethylene/polypropylene (PE/PP), sheath-core bicomponent fibers may be employed to form the bicomponent fiber portion of any of the described fabrics. Suitable PE/PP bicomponent fibers are available from Chisso Corp., a business having offices in Osaka, Japan.

Bodyside, liner layer 80 includes at least about 90 wt %, and preferably 100 wt %, of bicomponent fibers to provide desired levels of tactile softness and abrasion resistance. The bodyside layer has a basis weight of at least about 10 gsm, and the bicomponent fiber size is within the range of about 0.9–3 denier with a fiber length within the range of about 1–3 in. Preferably, the fiber denier is within the range of about 1.5–2.5, and more preferably, is about 1.8 denier. A preferred fiber length is about 1.5 in. For example, bodyside layer 80 may comprise a carded web which has a basis weight of about 17 gsm and is composed of 100% PET/polyethylene, sheath-core bicomponent fibers, obtained from BASF Corp., with a fiber denier of about 1.8 and fiber lengths of about 1.5 in.

In a particular embodiment of composite surge management portion 76, outerside layer 78 forms approximately 65 weight percent of the composite web and is composed of a blend of polyester fibers and bicomponent fibers. With respect to this blended outerside layer, about 60 weight percent of the blended layer is composed of polyester fibers of at least about 6 denier and with a fiber length within the range of about 1.5–2 inches. The remaining 40 percent of the blended layer is composed of bicomponent fibers of not more than about 3 denier, and preferably about 1.8 denier, with fiber lengths within the range of about 1.5–2 inches. Bodyside layer 80 comprises the remaining 35 weight percent of the composite web, and is composed of bicomponent fibers having a denier within the range of about 0.9–3 to provide a soft liner type material appointed for placement against a wearer's skin. In a particular embodiment, the bodyside layer of the composite web has a basis weight of about 15 gsm and is composed of bicomponent fibers of about 2 denier.

Another embodiment of composite web 76 can comprise a bodyside layer 80 composed of about 100% polyethylene/polyester sheath-core bicomponent fibers of not more than about 3 denier. The bodyside layer has a basis weight of about 15 gsm. In addition, this embodiment of composite web 76 includes an outerside layer composed of a 50/50 blend of polyester fibers of about 6 denier and polyester/ polyethylene, sheath-core bicomponent fibers of not more than about 3 denier.

In the various embodiments of the invention, the surge layer width is within the range of about 16–100% of the topsheet width. The surge layer width is preferably at least about 24% of the topsheet width, and more preferably, is at least 50% of the topsheet width to provide desired levels of effectiveness.

The various embodiments of surge management portion 46 may extend over the complete length of retention portion 48, or may extend over only a part of the retention portion length. Where the surge management portion extends only partially along the length of the retention portion, the surge management portion may be selectively positioned anywhere along absorbent structure 32. For example, surge management portion 46 may function more efficiently when it is offset toward the front waistband of the garment and transversely centered within front section 40 of absorbent structure 32. Thus, surge management portion 46 can be approximately centered about the longitudinal center line 58 of absorbent structure 32, and positioned primarily in central region 54 of front section 40 of absorbent structure 32. In the illustrated embodiment, none of surge management portion 46 is located in ear regions of 50 and 52.

The generally forward, offset positioning of surge management portion 46 can be defined by specifying the percentage of the top surface area of surge management portion 46 which is found forward of a particular reference point, such as transverse centerline 24, along the length of absorbent structure 32. The positioning of surge management portion 46 can alternatively be defined with respect to the volume or weight percent of the surge management portion which is positioned forward of a reference point.

The surge management portion and the topsheet layer each have an effective average pore size. In constructions where the surge management portion is located adjacent the outerside of the topsheet, the effective average pore size of the surge management material is preferably smaller than the effective average pore size of said topsheet material, and the material of the surge management portion is preferably more hydrophilic than the topsheet material.

Due to the high concentration of high absorbency material and the thinness of retention portion 48, it has also been desirable to mask the appearance of the soiled absorbent. One arrangement for increased masking is to reduce the light transmission of backsheet 30 to a transmission rate within the range of about 25–40 percent, as measured by a XL 211Hazegard System (Gardner) available from Pacific Scientific of Silver Springs, Md. or an equivalent measuring device.

For example, the opacity of backsheet 30 may be increased by incorporating $TiO_2$ (titanium dioxide) or other types of pigments into the formulation of a polyethylene backsheet material. In particular arrangements of the invention, backsheet 30 is composed of a polyethylene film having a thickness within the range of about 1.0–2.0 mil.

An alternate arrangement for providing increased masking is to interpose a substantially nonwettable, pigmented web 72 between the retention portion and the backsheet. For example, web 72 may comprise a meltblown web composed of polyolefin fibers pigmented with about 10 weight percent $TiO_2$ pigment. The nonwettable characteristic of web 72 helps reduce the amount of liquid contacting backsheet 30 and thereby helps reduce the visibility of the soiled absorbent.

Figure 8:
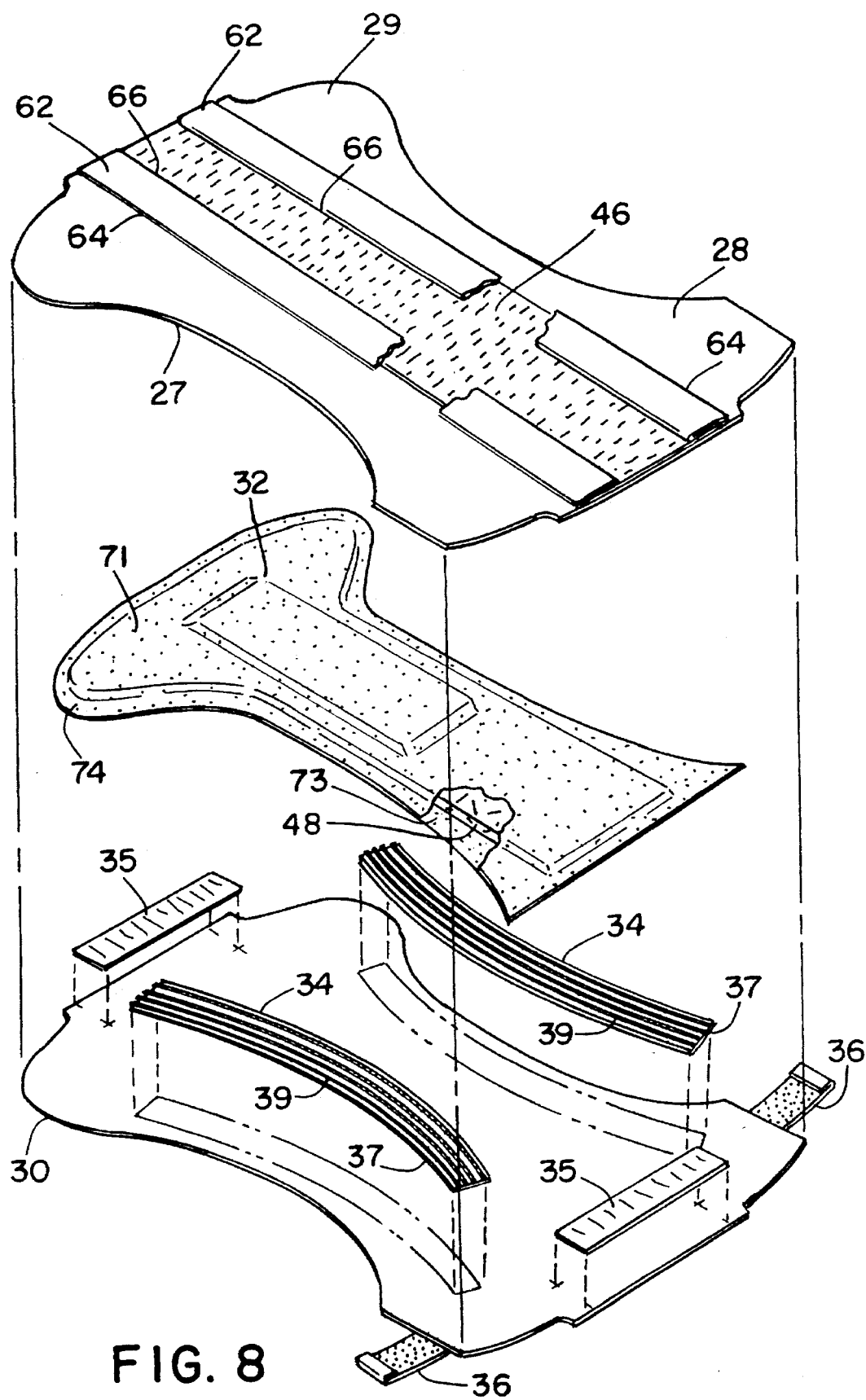
FIG. 8 representatively shows an exploded, perspective view of the article of FIG. 5.

With reference to FIGS. 8 and 9, the absorbent structure of the present invention may advantageously comprise an integrally formed arrangement composed of non-uniform, differentially-configured fibrous sections wherein particular component sections, such as surge management portion 46 and retention portion 48, include fibers which are interwoven or otherwise entangled together at the fibrous interfaces between the components. Such an arrangement can advantageously improve the effectiveness of the liquid transport from the surge management portion and into the retention portion.

It is contemplated that a surge management portion constructed in accordance with the present invention will be tailored and adjusted to accommodate various levels of performance demand imparted during actual use. For example, mild urinary incontinence and menstrual flow pads involve different delivery rates, volumes and timing than infant urine insults. Moreover, the liquid in the surge can vary in terms of the liquid viscosity, surface tension, temperature, and other physical properties which could affect the performance of the fabric in the various actual product end usages.

With respect to absorbent articles, wherein reduced bulk or reduced cost may be important, the surge management and retention portions need not extend over the entire, overall shape of the garment. Rather, they could be generally configured and located to cover only the genital region of the wearer, and both the surge management portion and the retention portion could be offset toward the front section of the garment outer cover 30.

It has been found that an effective fabric for constructing the surge management portion can be distinctively characterized by particular distinctive parameters. Such parameters include, for example, compressibility, resiliency, basis weight, pore size and void volume. Further parameters can include: (a) a pore size structure which will allow for rapid liquid intake and desorption while creating a restraining force which restricts uncontrolled, random movement of the liquid; (b) a bonding matrix which will help stabilize the pore size structure; (c) a gradient pore size structure; and (d) a gradient contact angle structure.

A compressible fabric structure will deform under the loads typically imparted by a wearer, and can provide a soft, cushiony feel. In particular aspects of the invention, the surge management portion when dry can compress to less than about 25% of its original, uncompressed thickness when subjected to a pressure of 2 psi (13.8 kPa).

A resilient fabric structure allows the fluid surge management portion of the present invention to:

(1) stay open under load, to maintain void volume in the fabric;

(2) resist collapsing when wetted to better release liquid and to better allow the fabric to be desorbed; and (3) be regenerating after being wetted to preserve void volume capacity for successive insult(s).

For increased ability to maintain desired pore structures, the surge management material can be constructed to have a selected level of resistance to compression. More particularly, in one aspect of the invention, the surge management material has a density, when dry, of not more than about 0.08 gm/cc, as measured at 1.0 psi. In a further aspect of the invention, the surge management material also exhibits a density, when wet, of not more than about 0.08 gm/cc, as measured at 1.0 psi.

The ability to maintain an open structure under load can be further represented by the ability of the wet material to recover its original thickness after being compressed. Preferred materials exhibit an ability to recover a large proportion of their original thickness after being compressed even when the material is wet.

To determine the effect of extended wet compression on a surge material, a wet sample is compressed at a pressure of 2.0 psi for 60 minutes and then measured for density at the 2.0 psi loading. The sample is then also measured for density at a loading of 0.2 psi. The wet resilience factor is determined by dividing the sample density at 2.0 psi by the sample density at 0.2 psi. In a particular aspect of the invention, the surge management material exhibits a wet resilience factor of at least about 1.5. Preferably, the surge management material has a wet resilience factor of at least about 1.7 to provide improved benefits.

With the various embodiments of the invention, the basis weight of surge management portion 46 is at least about 17 grams per square meter (gsm), preferably is at least about 24 gsm, and more preferably is at least about 40 gsm to help provide the total void volume capacity desired for effective operation. In a particular aspect of the invention, the basis weight is within the range of about 17–102 gsm, and preferably, is within the range of about 24–68 gsm to provide further advantages. In a further aspect of the invention, the surge management portion has a basis weight which is within the range of about 40–60 gsm, and preferably, is within the range about 45–55 gsm to provide improved effectiveness. In a particular embodiment, the basis weight is about 50 gsm.

The amount of basis weight can be important for providing a total holding capacity which is adequate to temporarily retain the amount of liquid that is typically discharged by a wearer during a single surge/insult of liquid into the absorbent article. For instance, a basis weight which is too low can result in excessive pooling of liquid against the wearer's skin or excessive run-off of liquid.

It will be readily apparent that absorbent articles requiring more surge capacity may also require proportionally greater amounts of surge management material. The surge management material, however, need not be of uniform basis weight throughout its areal extent, but instead can be arranged so that some sections have more surge management material compared to other sections. For the purposes of the present invention, the effective basis weight will be the weight of the surge management material divided by the area over which the surge management portion extends.

Liquid ordinarily flows along fiber surfaces, and the fiber surfaces are the usual transport routes to the void volume defined by the interfiber spacings of the fabric structure. By properly selecting the amounts and spatial arrangements of the wettable and nonwettable fiber surface areas per standard unit of fabric, the fluid access to the void volume of the material can be improved without adversely affecting the fluid release characteristics. A preferred fabric for the surge management portion can comprise a generally homogeneous blend of fine small diameter fibers intermingled with stiffer, larger diameter fibers. The large denier fibers can provide for the formation of relatively large pores that act as containers or reservoirs for the liquid. The small denier fibers can provide for the creation of relatively small pores that tend to restrain, fence in or hold onto the liquid, thereby preventing unrestricted run-off flow within the fabric structure.

The finer the fiber size, the greater the available surface area per unit weight. Therefore, increased surface area is generally provided by using more fibers and finer fibers. High amounts of wettable surface area per unit weight of fabric can also be provided by fibrous webs composed of relatively large fibers with a high wettable surface area per unit weight, e.g. wood pulp fluff fibers. Although larger, stiffer fibers can enhance the ability of the material to maintain the desired structure when wetted and subjected to compressive forces, such as the compressive forces typically applied by the wearer of the garment during use, they may adversely affect tactile properties of the fabric and may not adequately increase the fiber surface area.

The surge management portion can be a mixture of wettable and nonwettable fibers or can be composed entirely of wettable fibers. An appropriate fabric for the surge management portion can be configured to have a selected amount of wettable fiber surface area to (a) initially attract liquid into the fabric structure, (b) help provide rapid fluid uptake, and (c) help fill the void volume capacity of that fabric structure.

Wettable fiber surface area can be provided by employing naturally wettable fiber components with measured contact angles of less than 90° in the fabric structure of the surge management portion. Such fiber materials include cotton, rayon and wood pulp. Other suitable fiber materials can be inherently wettable synthetic polymers; hydrophilized or surface treated polymers, etc.; or materials having permanent, i.e, non-migratory, surface treatments applied to nonwettable substrate materials, for example, polypropylene, to reduce the contact angle below 90°.

In the various configurations of the absorbent article, such as diaper 10, the surge management portion is configured to cooperate with the other diaper components, such as top sheet 28 and retention portion 48, to provide for a rapid uptake of liquid discharges from the wearer. The rapid uptake of liquid can be characterized by liquid Penetration Rate index. More particularly, surge management portion 46 helps provide for a diaper Penetration rate index which is not less than about 2.67 m/sec. In addition, the exhibited penetration index is not more than about 10 ml/sec to provide improved effectiveness. Preferably, the Penetration Rate index is within the range of about 3.2–8 ml/sec, and more preferably, is within the range of about 4–5.33 ml/sec to provide desired benefits.

The surge management portion can also be configured to cooperatively provide for a Flowback index of not more than about 12 gm. Preferably, the Flowback index is not more than about 8 gm, and more preferably the exhibited Flowback index is not more than about 6 gm to provide improved benefits.

A suitable test for determining the Penetration Rate index and the Flowback index of an absorbent article is the Forced Intake and Flowback Evaluation (FIFE) test described in U.S. patent application Ser. No. 07/757,778 of D. Proxmire et al. and entitled "ABSORBENT ARTICLE HAVING A LINER WHICH EXHIBITS IMPROVED SOFTNESS AND DRYNESS, AND PROVIDES FOR RAPID UPTAKE OF LIQUID" (Attorney Docket No. 9932), now U.S. Pat. No. 5,192,606 issued Mar. 6, 1993 which was filed on even date herewith and is hereby incorporated by reference.

In a further aspect of the invention, the surge management portion can be further configured to cooperatively provide for a Whole Article Flowback (WAF) index of not more than about 0.7 gm. Preferably, the Whole Article Flowback index is not more than about 0.4 gm, and more preferably the exhibited WAF index is not more than about 0.3 gm to provide improved benefits. A suitable technique for determining the WAF index is the Whole Article Flowback index set Forth below in the TEST PROCEDURES section.

It has been found that each incidence of liquid discharge or surge should "linger" in the fabric structure of the surge management portion to temporarily occupy at least a part of its void volume capacity, instead of simply passing through in a relatively straightline path. A conventional layer of material with relatively large pore sizes can allow a substantially uninterrupted passage of liquid in a generally straight-line path without lingering in the structure prior to its release from the structure. In addition, the large pore sizes may provide insufficient restriction to sideways movement of liquid through the material along the plane of the material layer. As a result, the liquid may run off to the sides of the layer and leak from the article before the absorbent retention material can gather and contain the liquid. Such undesired, excessive run off may become more apparent when the absorbent material has already absorbed one or more previous discharges of liquid.

To help provide an advantageous combination of rapid liquid uptake, and desired levels of liquid lingering with suitable restriction of sideways movement of liquid, the material of surge management portion 46 can be configured with at least about 70% of its pore volume, per gram of surge material, is composed of pores having an effective pore size which is within the range of about 40–220 micrometers. Preferably, at least about 60% of the pore volume is composed of pores having an effective pore size is within the range of about 60–180 micrometers, and more preferably, at least about 40% of the pore volume is composed of pores having an effective pore size within the range of about 80–140 micrometers. If the effective pore size is too small, the rate of liquid penetration into the retention portion may be too slow, and if the pore size is too large, there may be insufficient restriction of sideways flow of liquid through the surge management portion.

Thus, the distinctive pore size distribution within the surge management portion of the invention can advantageously provide for a sufficiently rapid uptake of the liquid surges delivered onto the target zone, and also allow a controlled spreading of the liquid through the void volume of its structure to temporarily fill it. The liquid surge can effectively "linger" in the fabric structure to occupy the void volume for a discrete, transitional period instead of simply passing directly through in a generally straight-line path or gushing in a substantially unrestricted fashion, laterally along the general plane of the fabric. After an initial short period of time, the surge management portion can then be desorbed through the cooperative operation of the underlying or otherwise adjacent liquid retention portion.

A suitable method and apparatus for determining the effective pore size of surge management layer 46 and for generating data to compare pore sizes relative to the surge layer is described in detail in an article by A. A. Burgeni and C. Kapur, "Capillary Sorption Equilibria in Fiber Masses", Textile Research Journal (May 1967), Vol. 37, p. 356.

The effective pore size is considered to be the radius of the capillaries that would generate a capillary pressure (suction) equivalent to the hydrostatic tension measured by the Burgeni testing device. For example, see the discussion of equivalent capillary pore radius (diameter) set forth at page 362 and summarized in FIG. 6 of the Burgeni article. The correlation between capillary radius and capillary pressure can be determined from the following formula:

$$\rho * g * h = (2 \gamma \cos \theta)/r$$

where:

$\rho$=density of the liquid employed for testing $g$=gravitational acceleration (9.8 m/sec$^2$)

$h$=height difference measured by the Burgeni test $\gamma$=surface tension (dynes) of the liquid employed for testing $\cos \theta$=cosine of contact angle between the sample material and the testing liquid $r$=equivalent capillary (pore) radius The Burgeni technique can advantageously be automated by employing a movable VELMEX stage linked to a programmable stepper motor, an electronic balance and a microcomputer controller. The reservoir of testing liquid is held on the electronic balance, and the test sample funnel assembly is carried on the VELMEX stage. Data from the electronic balance is directed into the microcomputer, and the computer is programmed to move the stage to selected height positions. A suitable control program can be easily written to automatically activate the stepper motor to move the stage to a desired height, collect data at a chosen sampling rate until equilibrium occurs, and then move on to the next calculated, desired height. Absorption, desorption or both can be chosen in addition to sampling rates, equilibrium criteria, number of absorption/desorption cycles. The program can be readily configured to scan at constant pore radius interval or constant height interval, with the thickness of the sample being monitored constantly by a suitable instrument, such as a LVDT thickness transducer. The transducer converts distance moved into a voltage signal which can be processed by the computer. All raw data can be recorded on disk for later retrieval and data analysis. The liquid employed for the testing (e.g. water, synthetic urine, mineral oil) can easily be changed. It can be convenient to select a testing liquid which exhibits a substantially zero degree contact angle with the material of the test sample. Loading on the web sample can be varied to study external pressure effects on absorbency. After entering the desired experimental parameters and introducing the sample, the apparatus can proceed automatically until the completion of the run, with all raw data recorded on disk. Data analysis can be done with LOTUS or STATGRAPHICS software. A typical run can take 1–2.5 hr, depending upon the type of sample. Examples of suitable equipment components are as follows:

Digital balance: Scientific Micro Products, 1.0 mg precision; Serial interface, 300 baud.

Stage: Velmex Slide.

Stepper Motor: 200 steps per revolution, coupled to a drive screw which provides a drive advance of 1 inch per 10 revolutions.

Stepper Motor Controller: Smart Stepper, RS-232 interface.

LVDT: Schaevitz, Type 500 DC-D.

AD/DA Converter: Data Translation DT 2801, analog-to-digital or digital-to-analog converter.

Microcomputer: IBM-PC, 2 serial ports.

For the purpose of deriving effective pore sizes for the present specification, as determined from equivalent capillary radius, the test sample was 2.75 inches in diameter, and the testing liquid was mineral oil, such as Penetek technical grade mineral oil from Penreco, a business having offices in Los Angeles, Calif. The mineral oil has a viscosity of 5 centipoise, a surface tension of 32 dynes and a density of 0.81 gm/cc. The test was configured to evaluate the sample in the desorption mode, and the computer was set up to evaluate equivalent capillary pore radii ranging from 20 micrometers to 520 micrometers, scanning at 20 micrometer increments. The time between the taking of individual weight readings from the electronic balance was 20 sec. Four consecutive weight readings had to be within 0.05 gm before the computer indexed to the next pore radius increment. During testing, the sample of test material was restrained under a 0.015 psi loading. Pore volume (void volume), e.g. cubic centimeters per gram of sample weight, can be plotted as a function of the equivalent pore radii selected for evaluation by the computer. The total area under the plotted curve represents the total void volume per gram of sample. Accordingly, the area fraction, e.g. area percent, under the section of the plotted curve for a selected range of pore radii would represent the fraction, e.g. percentage, of pores having that range of equivalent capillary radii, per gram of sample.

In constructions of the invention where surge management portion 46 is located on the bodyside surface of topsheet 28, the soft tactile Feel of the surge management material can be enhanced by providing the material with a lofty, fuzzy bodyside surface. The fuzzy surface has a relatively large number of fibril networks 114 (FIG. 15) composed of fibrils 112, such as fibers and filamentary loops and arches, that project away from and extend above the base fabric 118 of the surge material. In particular aspects of the invention, the surge management material has a Perimeter per Edge Length (PPEL) index of at least about 5 (mm/mm). The PPEL index is preferably at of least about 5.5, and more preferably, is at least about 6 to provide improved tactile properties. A suitable technique for determining the PPEL index is set forth in the TEST PROCEDURES section below.

TEST PROCEDURES

Whole Article Elastic Tension Test
Equipment and materials:
1. Test equipment: Tensile tester, such as INSTRON Model 1130, with a SINTECH automated tensile testing system. The SINTECH system automates the tensile tester, and collects and processes the stress-strain data. SINTECH is a business located in Cary, N.C. 27513.
2. Tension cell, 20 kg.
3. Pneumatic action grips equipped with 10 in×1 in×0.25 in jaws, the faces of which are covered with a non-slip surface.

Specimen preparation:
1. INSTRON settings:
   Crosshead speed=250 mm/min;
   Full scale load=1000 gm;
   Initial gage length=6 inches; Number of cycles=2;
   Cycle termination at 1,000 gm load.
2. Where the product is removed from its package in a condition which is folded essentially in half, end-to-end, long a single fold line to produce a two-panel, folded configuration, maintain the product in its initial, two-panel fold condition to avoid the leg elastics. Where the product is delivered from its package in a condition which is folded end-to-end, along two or more fold lines to produce three or more panels, carefully reposition the product into a two-panel fold condition while minimizing any opening action which stretches the leg elastics. Cut off the longitudinal ends of the diaper along the width-wise edge of the absorbent core with a scissors.

Testing procedure:
1. Without disturbing the end-to-end, two-panel fold, unfold the ears of the article, if any.
2. Insert the back waistband end of the article into the lower jaw of the INSTRON, aligning the edge of the absorbent core with the bottom edge of the jaw.
3. Insert the front waistband end of the article into the upper jaw of the INSTRON, aligning the edge of the absorbent core with the top edge of the jaw.
4. Press the UP button to start the crosshead in motion. The crosshead should reverse direction when a load of 1,000 grams is achieved. One cycle is completed when the crosshead returns to the initial gage length of 6 inch. After a second cycle, the test is complete.

Data Collection:
1. Record the load in grams at 80% of full elongation on the 1st and 2nd elongation cycle curves and the 2nd cycle retraction curve.
2. Full elongation is defined as the gage length at which the 1,000 gram load is reached.
3. The whole article elastic tension value is the load in grams at 80% of full elongation on the 2nd elongation cycle curve.

Whole Article Flowback Test

The whole article flowback test measures the amount of fluid that emerges from the "body side" of an article, such as a diaper, after pressure is applied to an article which has been loaded with a predetermined amount of fluid.

Equipment & Materials
1. Saturated Capacity (SAT CAP) Tester with Magnahelic vacuum gage and latex dam; Tester is described in the Forced Intake and Flowback Evaluation (FIFE) test described in U.S. patent application Ser. No. 07/757,778 of D. Proxmire et al. and entitled "ABSORBENT ARTICLE HAVING A LINER WHICH EXHIBITS IMPROVED SOFTNESS AND DRYNESS, AND PROVIDES FOR RAPID UPTAKE OF LIQUID" (Attorney Docket No. 9932) now U.S. Pat. No. 5,192,606 issue Mar. 6, 1993; particular at column 1, line 31 through column 26, line 36.
2. Latex dam replacement, 0.014 inch. Obtain from McMaster-Carr Supply Co., Chicago, Ill. 60680–4355.
3. Blotter paper, 120 lb, "Verigood" Obtain from James River, Neenah, Wis. 54956.
4. Nylon screen, ¼ inch mesh (i.e. window screen material); obtain from a hardware store.
5. Timer, readable to one second
6. Scissors
7. Graduated cylinder, 250 mL
8. Absorbent toweling/tissue
9. Balance, readable to 0.1 gram
10. Synthetic urine. Obtain from PPG Industries, Appleton, Wis. 54912.
11. Room with standard-condition atmosphere: Temperature=23°±1° C. (73.4°±1.8° F.) and Relative Humidity=50±2%.

Specimen Preparation
1. Cut blotter stock to 3.5×12 inches (89×300 mm) if it was not ordered precut.
2. Weight each diaper to the nearest 0.1 gram and record the diaper weight on the data sheet.
3. Cut the elastic on the diaper to permit it to lie flat, making sure that the side and end "seals" are not disturbed.
4. Record the synthetic urine lot number and surface tension on the data sheet.

Testing Procedure

1. Measure or weigh the required amount of synthetic urine into the 250 ml cylinder.

REQUIRED AMOUNT

| | Size: | |
|---|---|---|
| Small | Medium | Large/Ex. Large |
| 120 ml | 180 ml | 240 ml |

"Small" = diaper sized for use by a wearer weighing up to about 13 lbs; "Medium" = diaper sized for use by a wearer weighing from about 13 lbs up to about 23 lbs; "Large" = diaper sized for use by a wearer weighing from about 23 lbs up to about 35 lbs; "Ex. Large" = diaper sized for use by a wearer weighing more than about 35 lbs.

2. Carefully pour the prescribed amount of synthetic urine into the urine target point area of the absorbent pad or diaper. Do not allow the fluid to run off the diaper. The target point area is the specified number of inches measured from the front of the diaper at the edge of the fluff. See the following target point locations. The values are in inches.

TARGET POINT LOCATION AREAS

| | Small | Medium | Large | Ex. Large |
|---|---|---|---|---|
| Him | 3 | 4 | 4½ | 4½ |
| Her | 4¾ | 5¾ | 6 | 6 |
| Unisex | 4 | 5 | 5½ | 5¾ |

3. Place the diaper onto the absorbency tester with the poly side down on the tester's rigid screen. Place the nylon screen over the absorbent pad.

4. Place the dry latex dam over the pad and adjust the vacuum to 0.5 psi (13.8 inches water). Hold at this pressure for three minutes and then release the pressure.

5. Remove the nylon screen from the absorbent. Wait 15 minutes before putting the blotter on the diaper. Do not remove the diaper from the SAT CAP tester.

6. While waiting, wipe the dam with tissue or toweling to remove excess fluid.

6. Weigh the appropriately-sized dry blotter paper to the nearest 0.1 gram and record.

8. Place the blotter paper over the front edge of the absorbent pad directly on top of the body side liner. Place the dry rubber dam over the blotter paper and pad, and adjust the vacuum to 0.5 psi (13.8 inches water). Hold at this pressure for two minutes, then release the pressure, remove the dam, and remove and weigh the wet blotter paper to the nearest 0.1 gram and record.

9. The amount of fluid flowback is calculated thus:

Flowback (gm)=Wet blotter weight−Dry blotter weight

Perimeter per Edge length Test

Figure 15:
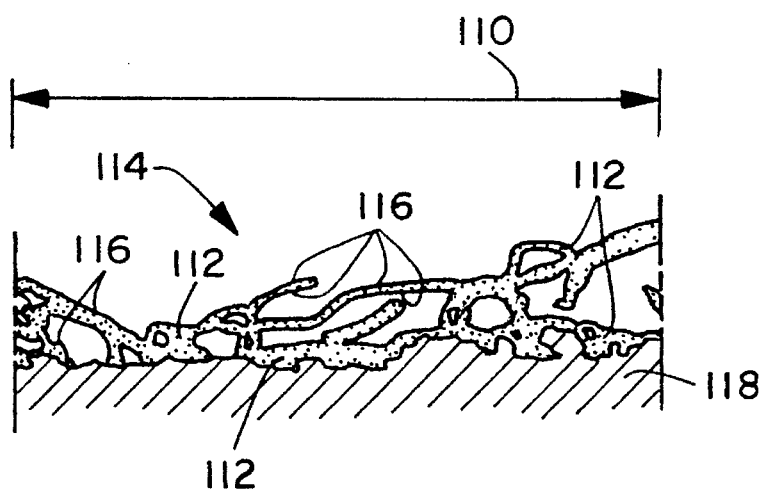
FIG. 15 representatively shows a fabric sample evaluated for PPL index.

FIG. 15 is a tracing of a magnified (10×) photograph of a sample of fabric material. The tracings represent a side view of the surface of the material as it is folded over a ¼ inch diameter stainless steel rod, showing the degree of fuzziness or nap exhibited by the surface of the material.

Figure 14:
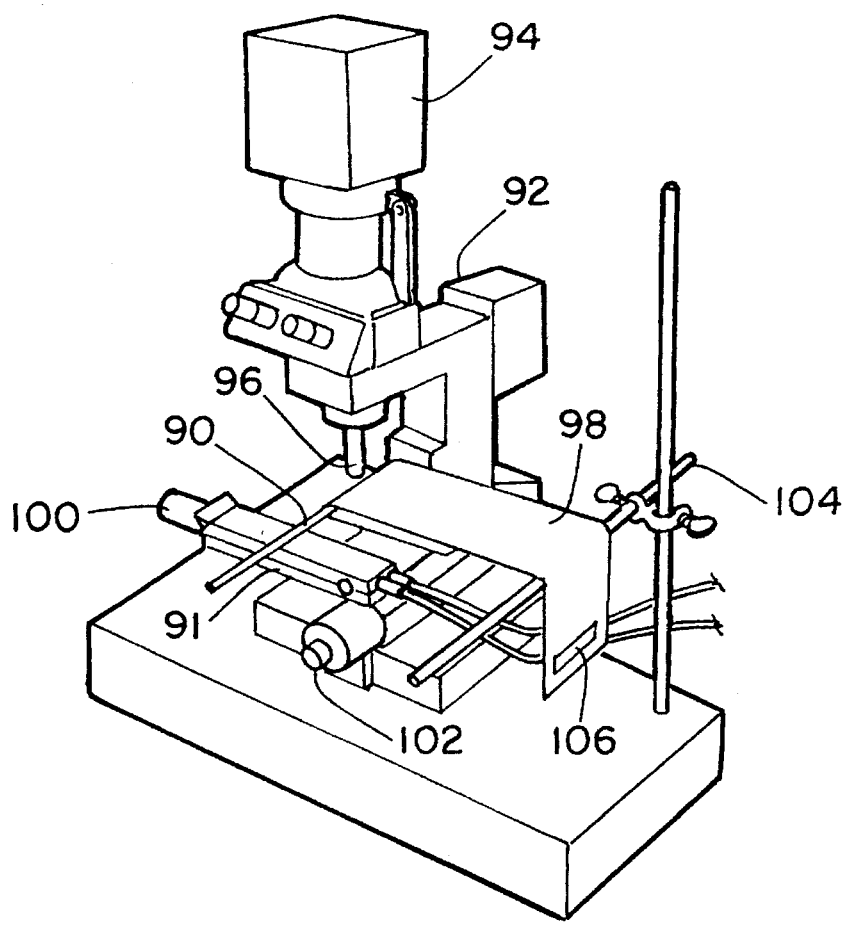
FIG. 14 representatively shows an apparatus suitable for determining the perimeter per edge length (PPL) index of a fabric.

FIG. 14 representatively shows a testing apparatus configured to measure the PPEL index. For photographing and measuring the degree of fuzziness, a ¼ inch diameter stainless steel rod 90 is attached to the "Y" motion portion of a 4 inch by 4 inch autostage 91 on a microscope 92, such as an Olympus BH-2 microscope. Stage motors 100 and 102 provide the X-Y movement of the auto stage. The microscope is the optical input for a scanner 94 attached to an image analyzer, such as a QMET 900 Image Analysis System available form Cambridge Instruments (LEICA Corp.). An Olympus 2× objective 96 (transmitted) with a Magchanger Image Amplifier at 1× was employed for viewing fabric sample 98. Sample backlighting was done without a condenser, with a fixed filter (10% transmission) and a variable neutral density filter ("Pol-Fader") on the condenser forks, positioned all the way up against the stage bottom. A field diaphragm of 0.5 was used. A material sample was cut into 5"×20" pieces and "fluffed up" with an air blast from a micropipette attached to a conventional laboratory air line (approximately 80 psi) and held about 2–3 inches away from the sample surface at an angle of about 45° and moved over the total sample surface in a "painting" motion during a period of about 5 sec. A 0.25 inch diameter rod, such as stainless steel rod 90, is suitably affixed to the top of the autostage in a substantially non-movable configuration. Sample 98 is taped down to the "X"-motion part of the stage, brought under rod 90, and positioned back over the stainless steel rod to hang over a draping bar, such as ½ inch diameter aluminum rod 104. A 67 gram weight 106 is taped to the hanging end of the sample. The surfaces of the liner are fluffed up again with the air blast to ensure reproducibility, and a 50-field scan is taken from each sample with only the fibril networks protruding from the bent edge being detected. The edges 116 of fibrils 114 are detected, with the fibril edges taken to correspond to gray levels of 10 to 50, on a gray scale 0–64 with the 2-D Autodelinerator ON. The lengths of the detected edges are summed to generate a total perimeter length For each field. Ten X-field edges and five Y-field edges are indexed. In each field, the total field perimeter length from detected fuzz is measured, and divided by the field height 110 (625-pixel frame height), which was 5.6612 mm (calibration factor=0.009058 mm/pixel). The resulting image analysis, using the combined data from both samples, yields a numerical perimeter per bent edge length (PPEL) representing the degree of fuzziness (nap) of each sample. A significant increase in PPEL correlates to an increase in perceived tactile softness.

The image analysis can be performed in accordance with the following program:

```
Cambridge Instruments QUANTIMET 900 QUIPS/MX: V03.02
ROUTINE: FLDFZ2    RUN: 0    SPECIMEN:
NAME = FLDFUZ
Enter specimen identify
Scanner    (No. 2 Newvicon LV = 4.82 SENS = 1.50)
CALL STANDARD
Load Shading Corrector (pattern - FLDFUZ)
Calibrate User Specified (Calibration Value = 0.009058
millimeters per pixel)
TOTFIELDS: = 0
TOTPROVEL: = 0
For SAMPLE = 1 to 2
Stage Scan    (              X           Y
           scan origin    15000.0      7000.0
           field size      7000.0      8000.0
           no of fields      10           5    )
Pause Message
PLEASE POSITION THE NEXT SAMPLE
Pause
Detect 2D    (Darker than 50 and Lighter than 10 PAUSE)
Amend        (CLOSE by 2)
For FIELD
Image Frame is Standard Live Frame
Live Frame is Standard Image Frame
Detect 2D (Darker than 50 and Lighter than 10)
```

```
Amend (CLOSE by 2)
Measure feature AREA PERIMETER X.FCP Y.FCP
    into array FEATURE (of 300 features and 5 parameters)
Accept FEATURE PERIMETER from 0.500 to 1000.
PROVEREL: = Field sum of FEATURE PERIMETER
PROVEREL: = PROVEREL/5.6612
Distribute COUNT vs PROVEREL into GRAPH
    from 0.00 to 10.00 into 20 bins, differential
TOTPROVEL: = TOTPROVEL + PROVEREL
TOTFIELDS: = TOTFIELDS + 1
Stage Step
Next FIELD
Next
Print " "
Print " "
Print Distribution (GRAPH, differential, bar chart, scale
    0.00)
Print " "
Print " "
Print "AVE PPEL =", TOTPROVEL/TOTFIELDS,
    "FOR", TOTFIELDS, "TOTAL FIELDS"
Print " "
Print " "
For LOOPCOUNT = 1 to 25
Print " "
Next
Print Distribution (HIST01, differential, bar chart, scale
    0.00)
For LOOPCOUNT = 1 to 25
Print " "
Next
End of Program
```

EXAMPLES

The following examples are presented to provide a more detailed understanding of the invention. The particular materials and parameters are exemplary, and are not intended to limit the scope of the invention.

Example 1

The surge management portion of Example 1 comprised a nonwoven fibrous web which included 75 percent polyester fibers of at least 6 denier, such as PET (polyethylene terephthalate) type 295 fibers available from Hoechst Celanese. The polyester fibers had a length ranging from about 1.5–2.0 inches in length. The remaining 25 percent of the fibrous web was composed of bicomponent binder fibers of about 1.5 denier. The bicomponent fiber length ranged from about 1.5–2 inches. A suitable bicomponent fiber is type ES-CHR4 wettable, polypropylene/polyethylene bicomponent fiber available from Chisso. The bicomponent fiber was a composite, sheath-core type with the polypropylene forming the core and polyethylene forming the sheath of the composite fiber. The polyester fibers and bicomponent fibers were generally homogeneously blended together and were not in a layered configuration. The fibers formed a carded web which was thermally bonded by through-air bonding.

Example 2

The surge management portion of Example 2 was composed of a through-air bonded carded web which had a basis weight of about 50 gsm and included a mixture of polyester (PET) single-component fibers and PET/polyethylene bicomponent, conjugate fibers. The PET fibers, obtained from Hoechst-Celanese, comprised about 60 wt % of the nonwoven fabric, and were about 6 denier with an average fiber length of about 2 in. The PET/polyethylene bicomponent fibers, obtained from BASF Corp., comprised about 40 wt % of the fabric, and were about 1.8 denier with an average fiber length of about 1.5 in. The PET formed the core and the polyethylene formed the sheath of the bicomponent fiber.

Example 3

The composite, bonded-carded-web of Example 3 provided a two-element surge management portion composed of a liner-surge material wherein the outerside surge layer formed approximately 65 weight percent of the composite web and was composed of a blend of polyester fibers and bicomponent fibers. With respect to this blended outerside layer, about 60 weight percent of the blended layer was composed of polyester fibers of at least about 6 denier and with a fiber length within the range of about 1.5–2 inches. The remaining 40 percent of the blended layer was composed of bicomponent fibers of about 1.8 denier, with fiber lengths within the range of about 1.5–2 inches. The bodyside, liner layer of the composite web comprised the remaining 35 weight percent of the composite web, and is composed of bicomponent fibers having a denier of about 1.8 d to provide a soft liner type material appointed for placement against a wearer's skin. The liner portion of the composite web had a basis weight of about 15 gsm and was composed of polyethylene/polyester, sheath-core bicomponent fibers of about 1.8–2 denier. The composite, liner-surge web was bonded by through-air bonding.

Example 4

The composite, liner-surge material of Example 4 comprised a bonded-carded-web. The web included an outerward-side surge layer which formed approximately 65 weight percent of the composite web and was composed of a blend of polyester fibers and bicomponent fibers. About 50 weight percent of the blended, outerside layer was composed of polyester fibers of at least about 6 denier and with a fiber length within the range of about 1.5–2 inches. The remaining 50 percent of the blended layer was composed of polyester/polyethylene, sheath-core bicomponent fibers of not more than about 3 denier, with fiber lengths within the range of about 1.5–2 inches. The bodyside, liner layer of the composite web was composed of about 100% polyethylene/polyester sheath-core bicomponent fibers of about 3 denier. The bodyside layer had a basis weight of about 15 gsm, and the composite web was bonded by through-air bonding.

Example 5

In Example 5, a medium size diaper comprised a 1 mil thick backsheet composed of polyethylene film, and an absorbent pad. The absorbent pad included about 10 grams of wood pulp fluff and about 10 grams of polyacrylate superabsorbent particulate material. The fluff and superabsorbent were arranged to provide a total, average basis weight of about 430 gsm and a density of about 0.15–0.30 gm/cc. The superabsorbent material was Hoechst Celanese IM 3900, or an equivalent thereof. The absorbent pad also included a wet-strength, cellulosic tissue which was placed about the mass of wood pulp fluff and superabsorbent particles. The tissue wrap had a weight of about 2.3 grams and a basis weight of about 16–21 gsm. The resultant absorbent pad was sandwiched between the backsheet and a topsheet composed of a spunbond web of polypropylene fibers. The topsheet material was sized to be substantially coextensive with the diaper backsheet, and was composed of polypropylene fibers having a fiber denier within the range of about 2.8–3.2 d. The fibers formed a nonwoven spunbond web having a basis web of about 22 gsm and a web density of about 0.10 gm/cc. A surge management layer, composed of a bonded carded web, was attached to the outerward side surface of the topsheet with a pattern of hotmelt adhesive. The surge management material had a width of about 4 inches and extended along the entire length of the diaper. The surge management layer employed for this Example was substantially the same as the through-air bonded-carded-web material employed to construct the surge management material of Example 1. The diaper exhibited a Penetration Rate index (third insult) of about 3.2 ml/sec (80 ml in 24.1 sec) and a Flowback index of about 5.8 gm.

Example 6

The medium size diaper of this Example 6 comprised a 1 mil thick backsheet composed of polyethylene film, and an absorbent pad. The absorbent pad included about 10 grams of wood pulp fluff and about 10 grams of polyacrylate superabsorbent particulate material. The fluff and superabsorbent were arranged to provide a total, average basis weight of about 430 gsm and a density of about 0.15–0.30 gm/cc. The absorbent pad also included a wet-strength, cellulosic tissue which was placed about the mass of wood pulp fluff and superabsorbent particles. The tissue wrap had a weight of about 2.3 grams and a basis weight of about 16–21 gsm. The resultant absorbent pad was sandwiched between the backsheet and a topsheet composed of a spunbond web of polypropylene fibers. The topsheet material was sized to be substantially coextensive with the diaper backsheet, and was composed of polypropylene fibers having a fiber denier within the range of about 2.8–3.2 d. The fibers formed a nonwoven spunbond web having a basis web of about 22 gsm and a web density of about 0.10 lin/cc. A surge management layer, composed of a bonded carded web, was attached to the outwardly facing, bodyside surface of the topsheet with a pattern of hotmelt adhesive. The surge management material had a width of about 4 inches and extended along the entire length of the diaper. The surge management layer employed for this Example was substantially the same as the bonded-carded-web material employed to construct the surge management material of Example 2. The diaper exhibited a Penetration Rate index (third insult) of 3.7 ml/sec (80 ml in 21.4 sec) and a Flowback index of about 4.6 gm.

Example 7

In Example 7, a medium sized diaper comprised a 1 mil thick backsheet composed of polyethylene film, and an absorbent pad. The absorbent pad included about 10 grams of wood pulp fluff and about 10 grams of polyacrylate superabsorbent particulate material arranged to provide total, average basis weight of about 430 gsm and average density of About 0.15–0.30 gm/cc. The absorbent pad also included a wet-strength, cellulosic tissue which was placed about the mass of wood pulp fluff and superabsorbent particles. The tissue wrap had a weight of about 2.3 grams and a basis weight of about 16–21 gsm. The resultant absorbent pad was sandwiched between the backsheet and a topsheet composed of a spunbond web of polypropylene fibers. The topsheet material was sized to be substantially coextensive with the diaper backsheet, and was composed of polypropylene fibers having a fiber denier within the range of about 2.8–3.2 d. The fibers formed a nonwoven spunbond web having a basis web of about 22 gsm and a web density of about 0.10 gm/cc. A surge management layer, composed of a bonded carded web, was attached to the bodyside surface of the topsheet with a pattern of hotmelt adhesive. Preferably, the adhesive was selectively applied to the peripheral, end and side regions of the surge layer at an add-on amount of about 0.15 gm. The surge management material had a width of about 4 inches and extended along the entire length of the diaper. The surge management layer employed for this Example was substantially the same as the through-air bonded-carded-web material employed to construct the surge management material of Example 3. The diaper exhibited a Penetration Rate index (third insult) of about 6.1 ml/sec (80 ml in 3.1 sec) and a Flowback index of about 3.1 gm.

Example 8

The medium size diaper of this Example 8 was constructed in accordance with Example 8, except that the surge layer was composed of the surge management material of Example 4. The diaper exhibited a Penetration Rate index (third insult) of about 7.7 ml/sec (80 ml in 0.5 sec) and a Flowback index of about 4.0 gm.

Example 9

Four fabrics were constructed and tested for pore size distribution. The fabrics were suitable for use as surge management materials.

Fabric A (BCW-1) was a through-air bonded carded web having a basis weight of 1.5 ounces per square yard (osy) and a density of 0.066 gm/cc (at 0.1 psi). 75 wt % of the web was composed of 6.0 d×2 inch, type 295 PET fiber obtained from Hoechst Celanese; and 25 wt % of the web was composed of 1.5 d×1.5 inch, polyethylene/polypropylene sheath-core bicomponent fiber obtained from Chisso ES.

Fabric B (BCW-2) was a through-air bonded carded web having a basis weight of 1.5 ounces per square yard (osy) and a density of 0.054 gm/cc (at 0.1 psi). 60 wt % of the web was composed of 6.0 d×2 inch, type 295 PET fiber obtained from Hoechst Celanese; and 40 wt % of the web was composed of 1.8 d×1.5 inch, polyethylene/PET sheath-core bicomponent fiber obtained from BASF.

Fabric C (BCW-3) was a two layer, through-air bonded carded web having a composite basis weight of 1.5 ounces per square yard (osy) and an overall density of 0.024 (at 0.1 psi). The web included a bodyside liner layer and an outward side layer. The liner layer had a basis weight of 0.5 osy, and was essentially 100% composed of 1.8 d×1.5 inch polyethylene/PET bicomponent fibers obtained from BASF. The outward side layer had a basis weight of 1.0 osy. 60 wt % of the outward side layer was composed of 6.0 d×2 inch, Type 295 PET fiber obtained from Hoechst Celanese; and 40 wt % of the outward side layer was composed of 1.8 d×1.5 inch, polyethylene/PET sheath-core bicomponent fiber obtained from BASF.

Fabric D (BCW-4) was a two layer, through-air bonded carded web having a composite basis weight of 1.5 ounces per square yard (osy) and an overall density of 0.027 gm/cc (at 0.1 psi). The web included a bodyside liner layer and an outward side layer. The liner layer had a basis weight of 0.5 osy was essentially 100% composed of 3.0 d×1.5 inch polyethylene/PET bicomponent fibers obtained from BASF. The outward side layer had a basis weight of 1.0 osy. 60 wt % of the outward side layer was composed of 6.0 d×2 inch, Type 295 PET fiber obtained from Hoechst Celanese; and 40 wt % of the outward side layer was composed of 1.8 d×1.5 inch, polyethylene/PET sheath-core bicomponent fiber obtained from BASF.

Figure 13:
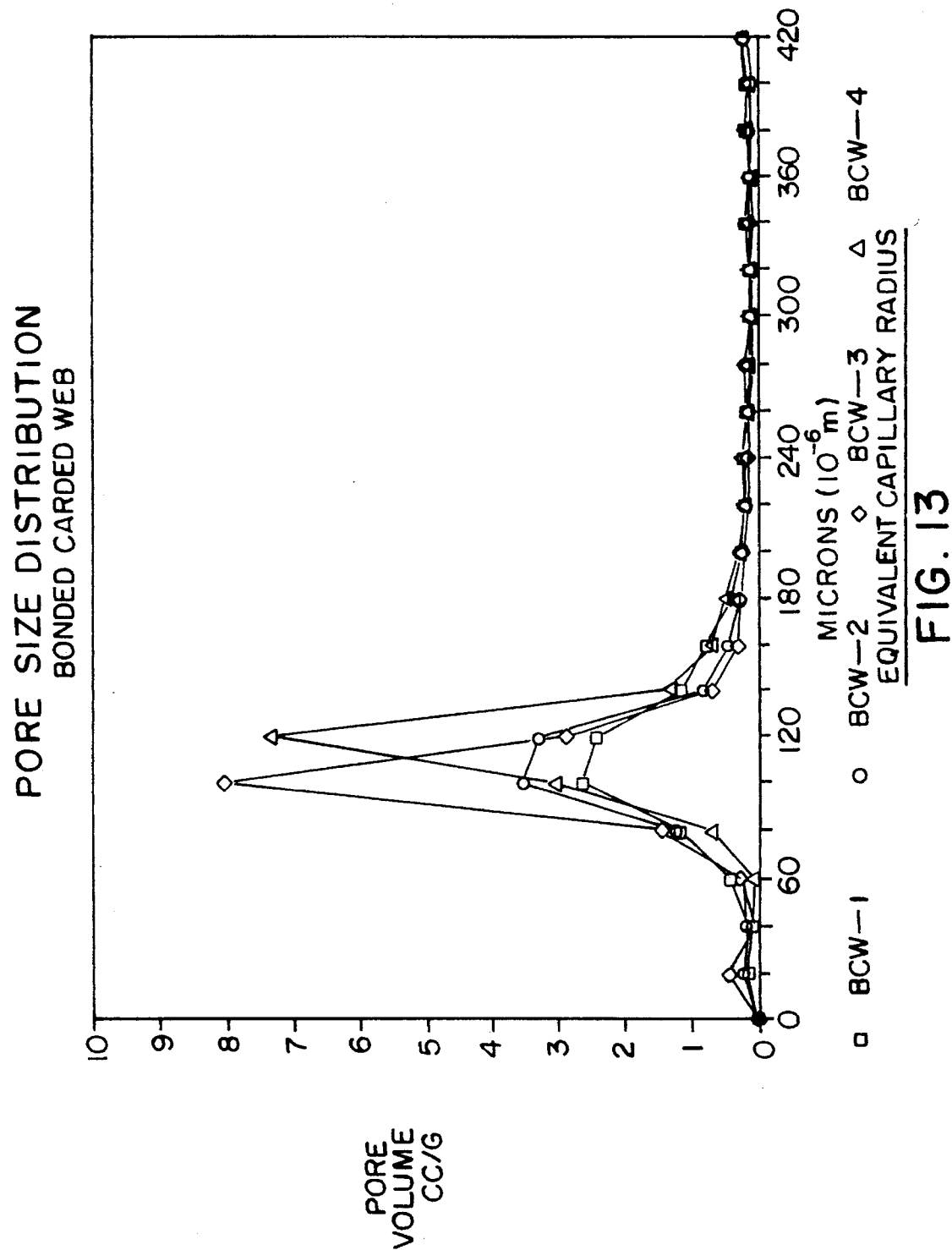
FIG. 13 is a graph which representatively shows the pore volume and pore size distribution for several nonwoven fabrics.

The pore size distributions were measured for each of the four fabrics and are illustrated in the graph of FIG. 13. For determining the pore radii, the test liquid was mineral oil and the term cos θ (cosine of contact angle) was considered to be equal to one.

Having thus described the invention in rather full detail, it will be readily apparent that various changes and modifications may be made without departing from the spirit of the invention. All of such changes and modifications are contemplated as being within the scope of the present invention, as defined by the subjoined claims.

We claim:

1. An absorbent article, comprising:

a backsheet layer;

a fibrous, liquid permeable topsheet layer for positioning against a wearer's skin, said topsheet layer having length and width dimensions and disposed in facing relation with said backsheet layer;

an absorbent retention portion which is interposed between said backsheet layer and topsheet layer, said retention portion having length and width dimensions smaller than corresponding dimensions of said topsheet layer and comprising a matrix of substantially hydrophilic fibers having a distribution of high-absorbency particle material therein, said hydrophilic fibers and high-absorbency particles provided in a fiber-to-particle ratio which is not more than about 70:30 and is not less than about 30:70 by weight;

a fibrous surge management layer which is arranged to transport liquid therethrough and includes bicomponent fibers having a denier of not more than about 3 d, said surge management layer having a facing surface thereof located in an adjacent, facing relation with at least one major, facing surface of said topsheet layer and thereby arranged to transport liquid between said facing surface of said surge management layer and said adjacent facing surface of said topsheet layer;

a multi-element wrapsheet which is located between said backsheet layer and said surge management layer and is placed adjacent major surfaces of said retention portion; said multi-element wrapsheet including a bodyside wrap layer and a separate outerside wrap layer, each of which extends past all or some peripheral edges of said fiber matrix to provide an outwardly protruding flange-type bonding region over which an entire or partial periphery of the bodyside wrap layer is connected to an entire or partial periphery of the outerside wrap layer.

2. An article as recited in claim 1, wherein said surge layer is arranged to provide a surge layer basis weight within the range of about 17–102 gsm, with about 0–75 wt. % of said surge layer composed of fibers having a denier of at least about 3 d with about 25–100 wt % of said surge layer composed of bicomponent fibers having a denier of not more than about 3 d.

3. An article as recited in claim 2, wherein said surge layer has a basis weight within the range of about 24–68 gsm.

4. An article as recited in claim 3, wherein said surge layer has a basis weight which is within the range of about 40–60 gsm.

5. An article as recited in claim 4, wherein said surge layer has a basis weight within the range about 45–55 gsm.

6. An article as recited in claim 1, wherein said surge management layer provides for a Penetration Rate index of not less than about 2.67 ml/sec and not more than about 10 ml/sec.

7. An article as recited in claim 6, wherein said surge management layer provides for Flowback index (FIFE) of not more than about 12 gm.

8. An absorbent article as recited in claim 1 wherein said high-absorbency particles provide a Deformation Under Load of not more than about 0.6 mm.

9. An absorbent article as recited in claim 8 wherein said high-absorbency particles provide an Absorbent Capacity (AC) of at least about 28 grams per gram.

10. An absorbent article as recited in claim 9 wherein said high-absorbency particles provide an Wicking Index (WI) of at least about 10 cm.

11. An absorbent article as recited in claim 1, wherein said surge management layer provides for a Fibril Projection index of at least about 5.

12. An absorbent article as recited in claim 1, wherein at least about 70% of the pore volume in said surge management layer is provided by pores having equivalent capillary radii within the range of about 40–220 micrometers.

13. An absorbent article as recited in claim 1, wherein at least about 60% of the pores within said surge management layer are within the range of about 60–180 micrometers.

14. An absorbent article as recited in claim 1, wherein at least about 40% of the pores within said surge management layer are within the range of about 80–140 micrometers.

15. An article as recited in claim 1, wherein said surge management layer is a nonwoven, bonded-carded-web, said web having a basis weight within the range of about 17–102 gsm and a density within the range of about 0.02–1.0 gm/cc, and said web including fibers having a denier within the range of about 0.9–18.

16. An article as recited in claim 15, wherein said web includes bicomponent fibers having polyethylene/polyester or polyethylene/polypropylene bicomponent structure.

17. An article as recited in claim 16, wherein said nonwoven, bonded-carded-web is composed of fibers having fiber lengths within the range of about 2.5–7.5 cm.

18. An article as recited in claim 17, wherein said web is a through-air-bonded-carded-web.

19. An article as recited in claim 17, wherein said web is an infrared-bonded-carded web.

20. An article as recited in claim 15, wherein said topsheet layer comprises a nonwoven spunbond web having a basis weight within the range of about 17–102 gsm and a density within the range of about 0.02–1.0 gm/cc.

21. An article as recited in claim 1, wherein said surge layer comprises a nonwoven bonded-carded-web which includes a fibrous bodyside layer and a fibrous outerside layer;

said body side layer having a basis weight within the range of about 10–34 gsm, and composed of polyethylene/polyester bicomponent fibers having a fiber denier within the range about 0.9–3.0 d;

said layer side layer having a basis weight within the range of about 24–44 gsm, and composed of a fiber blend, said blend comprising about 60 wt % of about 6 denier PET fibers and about 40 wt % of about 1.8 denier PE/PET or polyethylene/polypropylene bicomponent fibers.

22. An article as recited in claim 21, wherein said surge management layer is positioned on a bodyside surface of said topsheet.

23. An article as recited in claim 1, wherein said surge management layer comprises a nonwoven bonded-carded-web which includes said fibrous bodyside layer and fibrous outerside layer;

said body side layer having a basis weight within the range of about 10–34 gsm, and composed of bicomponent fibers having a fiber denier within the range of about 1.5–3.0 d;

said outerside layer having a basis weight within the range of about 24–44 gsm, and composed of a fiber blend, said blend comprising about 0–75 wt % of fibers having denier of about 3.0 d–18 d, and about 25–100 wt % of bicomponent fibers having denier of about 0.9–3 d.

24. An article as recited in claim 23, wherein said surge management layer is positioned on a bodyside surface of said topsheet.

25. An article as recited in claim 23, wherein said body side layer includes polyethylene/polyester bicomponent fibers.

26. An article as recited in claim 25, wherein said outer side layer fiber blend includes polyethylene/polyester bicomponent fibers.

27. An article as recited in claim 23, wherein said body side layer includes polyethylene/polypropylene bicomponent fibers.

28. An article as recited in claim 27, wherein the bicomponent fibers in said outer side layer fiber blend are polyethylene/polypropylene bicomponent fibers.

29. An article as recited in claim 1, wherein said retention portion comprises a mixture of woodpulp fluff and superabsorbent material, said superabsorbent material having a Deformation Under Load of about 0.60 millimeter or less, a Wicking Index of about 10 centimeters or greater and an Absorbent Capacity of about 28 grams per gram or greater.

30. An article as recited in claim 29, wherein said superabsorbent material has an Absorbency Under Load value within the range of about 25–40, and an Absorbent Capacity within the range of about 32–48.

31. An absorbent article as recited in claim 1, wherein said surge management portion and said topsheet layer each have an effective average pore size, wherein the effective average pore size of said surge management portion is larger than the effective average pore size of said topsheet layer.

32. An absorbent article as recited in claim 1, further comprising curved elastic members connected to said backsheet along longitudinally extending side edges thereof to provide elasticized leg gathers, each of said elastic members comprising a carrier sheet to which are attached a plurality of individual elastic strands.

33. An article as recited in claim 1, wherein said backsheet has a light transmission of not more than about 40%.

34. An article as recited in claim 1, further comprising a nonwettable, pigmented web interposed between said backsheet and said absorbent retention portion to provide for a light transmission of not more than about 40%.

35. An article as recited in claim 34, wherein said not wettable web comprises a meltblown web composed of polyolefin fibers.

36. An article as recited in claim 35, wherein said nonwettable meltblown web is pigmented with about 10 weight percent $TiO_2$ pigment.

37. An article as recited in claim 1, wherein said article provides for a whole article elastic tension of not more than about 250 gm.

38. An article as recited in claim 37, wherein said retention portion has a basis weight within the range of about 400–900 gsm and a thickness of not more than about 0.6 cm, and wherein said article provides for a whole article elastic tension value which is within the range of about 150–250 gm.

39. An absorbent article, comprising:

an absorbent retention portion which is located adjacent said backsheet layer, said retention portion comprising a matrix of substantially hydrophilic fibers having a distribution of high-absorbency particle material therein, said hydrophilic fibers and high-absorbency particles provided in a fiber-to-particle ratio which is not more than about 70:30 and is not less than about 30:70 by weight;

a surge management layer located over a body side surface of said retention portion, said surge layer comprising bicomponent fibers having a denier of not more than about 3 d, said surge layer constructed to provide for a liquid Penetration Rate index of not less than about 2.67 ml/sec, and said surge layer comprising a composite nonwoven bonded-carded-web which includes a fibrous bodyside layer portion an a fibrous outerside layer portion;

said body side layer portion having a basis weight within the range of about 10–34 gsm, and composed of bicomponent fibers having a fiber denier within the range of about 0.9–3.0 d;

said outer side layer portion having a basis weight within the range of about 24–44 gsm, and composed of a fiber blend, said blend comprising about 60 wt % of about 6 denier PET fibers and about 40 wt % of about 1.8 denier bicomponent fibers; and a multi-element wrapsheet which is located between said backsheet layer and said surge management layer and is placed adjacent major surfaces of said retention portion; said multi-element wrapsheet including a bodyside wrap layer and a separate outerside wrap layer, each of which extends past all or some peripheral edges of said fiber matrix to provide an outwardly protruding flange-type bonding region over which an entire or partial periphery of the bodyside wrap layer is connected to an entire or partial periphery of the outerside wrap layer.

40. An article as recited in claim 39, wherein said body side layer includes polyethylene/polyester bicomponent fibers.

41. An article as recited in claim 40, wherein said outer side layer fiber blend includes polyethylene/polyester bicomponent fibers.

42. An article as recited in claim 39, wherein said bicomponent fibers in said body side layer are polyethylene/propylene bicomponent fibers.

43. An article as recited in claim 42, wherein the bicomponent fibers in said outer side layer fiber blend are polyethylene/polypropylene bicomponent fibers.

44. An absorbent article, comprising:

a backsheet layer;

a fibrous, liquid permeable topsheet layer disposed in facing relation with said backsheet layer;

an absorbent retention portion which is interposed between said backsheet layer and said topsheet layer, said retention portion comprising a matrix of substantially hydrophilic fibers having a distribution of high-absorbency particle material therein, said hydrophilic fibers and high-absorbency particles provided in a fiber-to-particle ratio which is not more than about 70:30 and is not less than about 30:70 by weight, and said matrix defining a periphery having contoured side edges with inwardly bowed portions; and a fibrous wrapsheet located between said backsheet layer and said topsheet layer and placed immediately adjacent major surfaces of said retention portion, said wrapsheet including a bodyside wrap layer and an outerside wrap layer, each of which extends past all or some of the peripheral edges of said fiber matrix to provide an outwardly protruding, flange-type bonding region over which an entire or partial periphery of the bodyside wrap layer is connected to a periphery of the outerside wrap layer, said wrapsheet having curved side edges which are closed about said contoured edges of said matrix by said flange-type bonding region to seal said bonding region against migration of said high-absorbency particles.

45. An absorbent article as recited in claim 44, wherein said outerside wrap layer has a relatively lower basis weight than said bodyside wrap layer.

46. An absorbent article, comprising:

a backsheet layer;

a fibrous, liquid permeable topsheet layer which is disposed in facing relation with said backsheet layer;

an absorbent retention portion which is interposed between said backsheet layer and said topsheet layer, said retention portion comprising a matrix of substantially hydrophilic fibers defining peripheral edges and having a distribution of high-absorbency particle material therein, said hydrophilic fibers and high-absorbency particles provided in a fiber-to-particle ratio which is not more than about 70:30 and is not less than about 30:70 by weight; and a fibrous wrapsheet located between said backsheet layer and said topsheet layer and placed immediately adjacent major surfaces of said retention portion, said wrapsheet including a bodyside wrap layer and a separate outerside wrap layer, each of which extends past all or some of the peripheral edges of said fiber matrix to provide an outwardly protruding, flange-type bonding region over which an entire or partial periphery of the bodyside wrap layer is connected to a periphery of the outerside wrap layer, and said bodyside wrap layer having a relatively lower porosity than said outerside wrap layer.

47. An absorbent article as recited in claim 46, wherein said wrapsheet includes a hydrophilic material.

48. An absorbent article as recited in claim 46, wherein said outer side wrap layer has a relatively lower basis weight than said bodyside wrap layer.

49. An absorbent article as recited in claim 46, wherein said wrapsheet includes meltblown fibers.

50. An absorbent article as recited in claim 49, wherein said meltblown fibers are thermally bondable.

51. An absorbent article, comprising:

a backsheet layer;

a fibrous, liquid permeable topsheet layer for positioning against a wearer's skin, said topsheet layer having length and width dimensions and disposed in facing relation with said backsheet layer;

an absorbent retention portion which is interposed between said backsheet layer and topsheet layer, said retention portion having length and width dimensions smaller than corresponding dimensions of said topsheet layer and comprising a matrix of substantially hydrophilic fibers having a distribution of high-absorbency particle material therein, said hydrophilic fibers and high-absorbency particles provided in a fiber-to-particle ratio which is not more than about 70:30 and is not less than about 30:70 by weight;

a fibrous surge management layer located in an adjacent, facing relation with at least one major, facing surface of said topsheet layer, said surge layer having a fibrous bodyside layer and a fibrous outerside layer comprising bicomponent fibers having a denier of not more than about 3 d, said surge layer constructed to provide for a liquid Penetration Rate index of not less than about 2.67 ml/sec; and a multi-element wrapsheet which is located between said backsheet layer and said surge management layer and placed adjacent major surfaces of said retention portion, said multi-element wrapsheet including a bodyside wrap layer and a separate outerside wrap layer, each of which extends past all or some peripheral edges of said fiber matrix to provide an outwardly protruding, flange-type bonding region over which an entire or partial periphery of the bodyside wrap layer is connected to an entire or partial periphery of the outerside wrap layer, wherein said outerside wrap layer has a greater porosity than said bodyside wrap layer and wherein at least said bodyside wrap layer has a pore distribution wherein no more than about 5 percent of the pores, as measured by Coulter porometry, are greater than about 50 micrometers in diameter.

52. An absorbent article, comprising:

a backsheet layer;

a fibrous, liquid permeable topsheet layer disposed in facing relation with said backsheet layer;

an absorbent retention portion which is interposed between said backsheet layer and said topsheet layer, said retention portion comprising a matrix of substantially hydrophilic fibers having a distribution of high-absorbency particle material therein, said hydrophilic fibers and high-absorbency particles provided in a fiber-to-particle ratio which is not more than about 70:30 and is not less than about 30:70 by weight, and said matrix defining a periphery having contoured side edges with inwardly bowed portions; and a fibrous wrapsheet located between said backsheet layer and said topsheet layer and placed immediately adjacent major surfaces of said retention portion, said wrapsheet including a bodyside wrap layer and an outerside wrap layer, each of which extends past all or some of the peripheral edges of said fiber matrix to provide an outwardly protruding, flange-type bonding region over which an entire or partial periphery of the bodyside wrap layer is connected to a periphery of the outerside wrap layer, said bodyside wrap layer having a relatively lower porosity than said outerside wrap layer, and said wrapsheet having curved side edges which are closed about said contoured edges of said matrix by said flange-type bonding region to seal said bonding region against migration of said high-absorbency particles.

* * * * *